US007307137B2

(12) United States Patent
Lau et al.

(10) Patent No.: US 7,307,137 B2
(45) Date of Patent: Dec. 11, 2007

(54) LOW DIELECTRIC CONSTANT MATERIALS AND METHODS OF PREPARATION THEREOF

(75) Inventors: Kreisler Lau, Sunnyvale, CA (US); Feng Quan Liu, Cupertino, CA (US); Paul Apen, San Francisco, CA (US); Boris Korolev, San Jose, CA (US); Emma Brouk, San Jose, CA (US); Ruslan Zherebin, Daly City, CA (US); David Nalewajek, West Seneca, NY (US); Roger Leung, San Jose, CA (US)

(73) Assignee: Honeywell International Inc., Morristown, NJ (US)

( * ) Notice: Subject to any disclaimer, the term of this patent is extended or adjusted under 35 U.S.C. 154(b) by 239 days.

(21) Appl. No.: 10/466,651

(22) PCT Filed: Oct. 18, 2001
(Under 37 CFR 1.47)

(86) PCT No.: PCT/US01/32569

§ 371 (c)(1),
(2), (4) Date: Mar. 11, 2004

(87) PCT Pub. No.: WO02/081546

PCT Pub. Date: Oct. 17, 2002

(65) Prior Publication Data

US 2004/0158024 A1    Aug. 12, 2004

(51) Int. Cl.
*C08G 63/78* (2006.01)
(52) U.S. Cl. .................. 528/86; 528/205; 528/207; 528/208; 528/211; 525/132; 525/149; 525/152; 525/168; 525/177
(58) Field of Classification Search ............... 528/86, 528/205, 207, 208, 211; 525/132, 149, 152, 525/168, 178, 177
See application file for complete search history.

(56) References Cited

U.S. PATENT DOCUMENTS 3,580,964 A    5/1971    Driscoll .................. 260/871

(Continued)

FOREIGN PATENT DOCUMENTS

WO    WO00/40637    7/2000

OTHER PUBLICATIONS

E.S. Moyer, et al.; "Ultra Low k Silsesquixane Based Resins", Concepts and Needs for Low Dielectric Constant <0.15 um Interconnect Materials: Now and the Next Millenium, Sponsored by the American Chemical Society, pp. 128-146 (Nov. 14-17, 1999).

(Continued)

*Primary Examiner*—Duc Truong
(74) *Attorney, Agent, or Firm*—Sandra Thompson; Buchalter Nemer

(57) ABSTRACT

The present invention is directed to low dielectric polymers and to methods of producing these low dielectric constant polymers, dielectric materials and layers, and electronic components. In one aspect of the present invention, an isomeric mixture of thermosetting monomers, wherein the monomers have a core structure and a plurality of arms, is provided, and the isomeric mixture of thermosetting monomers is polymerized, wherein polymerization comprises a reaction of an ethynyl group that is located in at least one arm of a monomer. In yet another aspect of the inventive subject matter, spin-on low dielectric constant materials are formed having a first backbone with an aromatic moiety and a first reactive group, and a second backbone with an aromatic moiety and a second reactive group, wherein the first and second backbone are crosslinked via the first and second reactive groups in a crosslinking reaction preferably without an additional crosslinker, and wherein a cage structure having at least eight (8) atoms is covalently bound to at least one of the first and second backbone.

50 Claims, 16 Drawing Sheets

U.S. PATENT DOCUMENTS

| | | | |
|---|---|---|---|
| 4,756,977 A | 7/1988 | Haluska et al. | 428/704 |
| 5,225,586 A | 7/1993 | Parker et al. | 560/21 |
| 5,268,202 A | 12/1993 | You et al. | 427/255 |
| 5,370,903 A | 12/1994 | Mine et al. | 427/126.2 |
| 5,486,564 A | 1/1996 | Mine et al. | 524/588 |
| 5,658,994 A | 8/1997 | Burgoyne, Jr. et al. | 525/390 |
| 5,874,516 A | 2/1999 | Burgoyne, Jr. et al. | 528/219 |
| 5,900,290 A | 5/1999 | Yang et al. | 427/577 |
| 5,965,679 A | 10/1999 | Godschalx et al. | 526/281 |
| 5,986,045 A | 11/1999 | Lau et al. | 528/401 |
| 6,143,855 A | 11/2000 | Hacker et al. | 528/31 |
| 6,225,238 B1 | 5/2001 | Wu | 438/778 |
| 6,278,174 B1 | 8/2001 | Havemann et al. | 257/637 |
| 6,288,188 B1 | 9/2001 | Godschalx et al. | 526/285 |

OTHER PUBLICATIONS

Waeterloss et al.; "Integration Feasibility of Porous SiLK Semiconductor Dielectric". Proc. of the 2001 International Tech. Conf., pp. 253-254 (2001).

Reichert; "Rigid-Expanded Tetrahedral Cores for Four-Armed Branched Structures: 1,3,5,7-TEtrakis (4-Iodophenyl_ADA Manatane and its Derivatives"; 1993, vol. 34, Issue 1, pp. 495-496.

Mathias; "Synthesis of Macromolecules from 1,3,5,7-Tetra (4-Iodop Henyl) Adamantane: A New Core for Dendritic Molecules"; 1992, vol. 33, Issue 2; pp. 144-145.

Mathias; "Syntheseis of Rigid Tetrahedral Tetrafunctional Molecules from 1,3,5,7-Tetrakis (4-Iodophenyl) Adamantane"; 1993, vol. 5, Issue 1; pp. 4-5.

Mathias; "Adamantane-Containing Polymers"; 1996, vol. 624, pp. 197-207.

Acar; "Evaluation of the Adamantyl Effect on Vinyl Polymer TSUBg"; 1999, vol. 40, n. 2; pp. 620-621.

Van Reenen; "Polymeriazation of Alpha-Olefins with Bulky Pendant Groups: 3-(1-Adamantyl)-1-Porpene"; 1999, vol. 40, n. 2; pp. 577-578.

Lewis; "Thermal Behavior of Polymers with Pendent Adamanytl Grups Using DMTA"; 1996, vol. 37, No. 2; pp. 243-244.

Grubb; "Synthesis of Benzyl Ether Polymers Containing Pendant Adamantyl Groups and the Effect ofn Polymer Properties"; 1996, vol. 37, No. 1; pp. 551-552.

Mathias; "Adamantyl -Substituted Phenolic Polymers"; 1996; vol. 34; pp. 397-402.

Lewis; "A New Class of Poly (ether ether ketone)s based on Adamanytl-Substituted Bisphenols: Effects of Pendent Adamantyl Groupsl on Polymer Properties"; 1995; vol. 36, 2; pp. 140-141.

Mathias; "Linear and Start-Branched Siloxy-Silane Polymers: One-pot A-B Polymeriazation and End-Capping"; 1992; vol. 33 (2); pp. 146-147.

Reichert; "Highly Cross-Linked Polymers Based on Acetylene Derivatives of Tetraphenyladamantane"; 1994; vol. 27, No. 24; pp. 7030-7034.

Reichert; "Expanded Tetrahedral Molecules from 1,3,5,7-Tetrapheny Ladamantane"; 1994; vol. 27, No. 24; pp. 7015-7023.

Reichert; "Tetrahedrally Oriented Four-Armed Star and Branched Aramids"; 1994; vol. 24, No. 24; pp. 7024-7029.

Rutherford; Poly (2,5-Ethynylenethiophenediylethynylenes), Related Hetroaromatic Analogues and Poly (thiene )3,2-b) Thiophenes). Synthesis and Thermal and Eelctrical Properties; 1992; Vo. 25, No. 9; pp. 2294-2306.

Mathias; "Poly (D1-1-Adamantyl Fumarate). A thermally Stable Substituted Polymethylene"; 1991; vol. 24, No. 18; pp. 5232-5233.

Acar; "Evaluation of the Spacer Effect on Adamanante-Containing Vinyl Polymer TSUBg's"; 2000; vol. 33, No. 10; pp. 3855-3859.

Mathias; Poly (ether ether ketone)s and poly (ether sulfones) with pendent Adamantyl Groups; 1997; vol. 30, No. 19; pp. 5970-5975.

Mathias; "Synthesis, Characterization, and Cure of Allyl and Propargyl Functionalized Indene as a Thermoset Composite Matrix Resin"; 1998; vol. 68, No. 3; pp. 475-482.

Mathias, et al.; "Adamantane-Containing Polymers"; 1995; vol. 35(1); pp. 741-742.

Mathias, et al.; "Stars, Dendrimers and Hyperbranched Polymers: Towards Understanding Structure-Property Relationships for Single Molecule Contructs"; 1993; p. 312.

Grubb; "Benzyl Ether Polymers: Crystallinity and Pendant Adamantyl Effects"; 1997; vol. 35, No. 9; pp. 1743-1751.

Reichert; "Investigation of Derivatives and Polymers of 1,3,5,7-Tetraphenyladamante. (Dissertation)"; May 1994; vol. 55-06B.

Reichert; "Highly Cross-Linked Polymers Based on Acetylene Derivatives of Tetraphenyladamantane"; 1994; Chem Abstract 121: 256441.

Morgenroth, et al.; Dendritic and Hyperbranched Polyphenylenes via a Simple Diels-Alder Route: 1997; Chem Abstract 127; 346752.

Lau, et al; Low Dielectric Constant Organic Dielectircs Based on Pendant Cage-Like Structures; Chem Abstract 135; 304608.

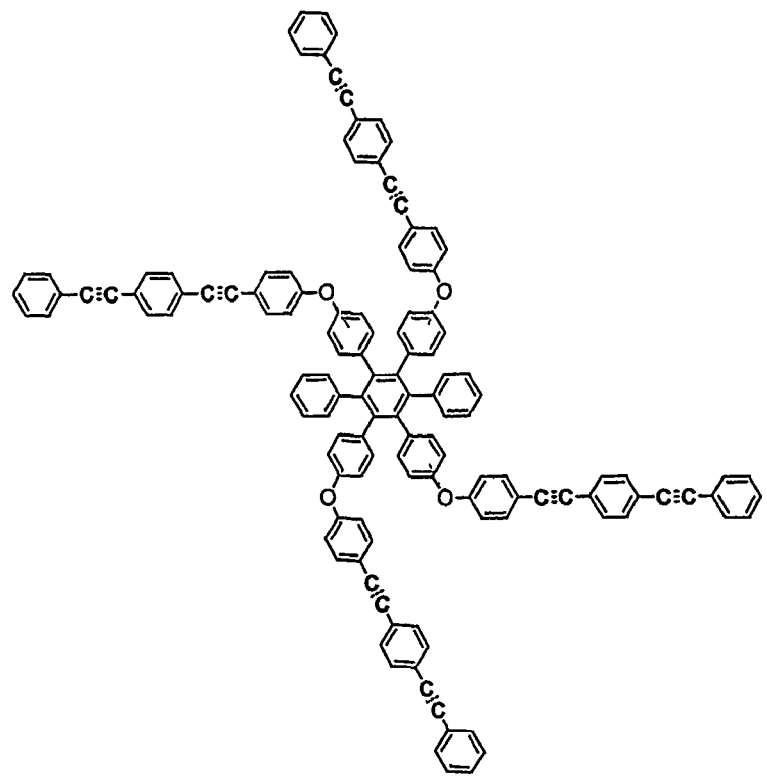
Figure 2A
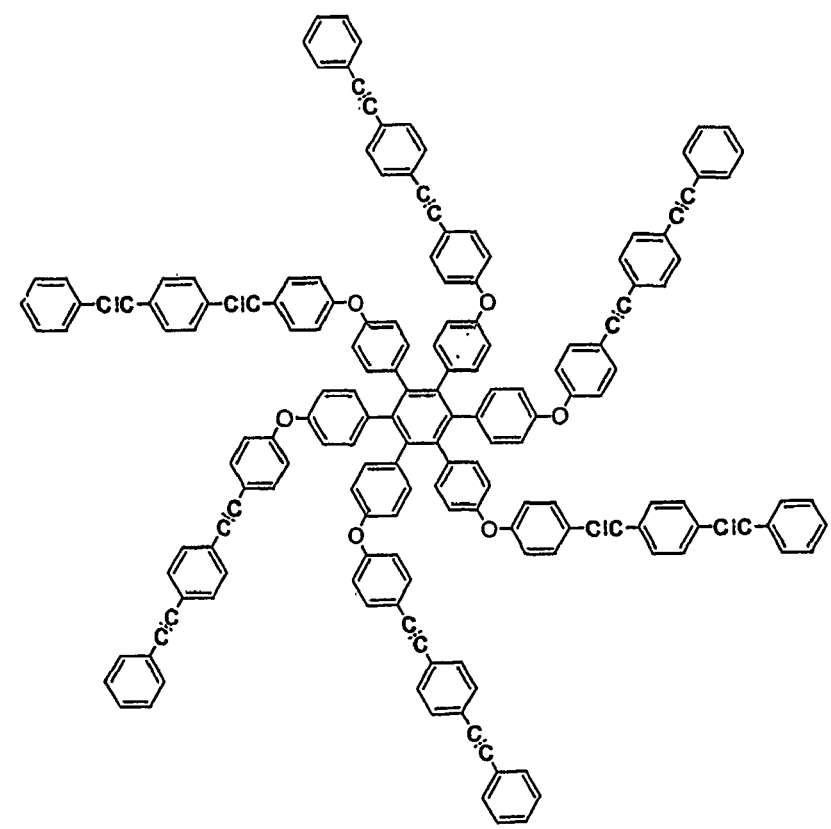
Figure 2.C

1,3,5,7-tetrakis(4'-iodophenyl)-adamantane
*p*-isomer 1,3,5,7-tetrakis[4'-(phenylethynyl)phenyl]-adamantane

LOW DIELECTRIC CONSTANT MATERIALS AND METHODS OF PREPARATION THEREOF

This application claims priority to following: PCT/US01/11273 filed on Apr. 6, 2001, U.S. Ser. No. 09/897,936 filed Jul. 5, 2001, U.S. Ser. No. 09/902,924 filed Jul. 10, 2001, and PCT/US01/22204 filed on Jul. 13, 2001 which are all incorporated herein by reference. This application is also related to U.S. Ser. No. 09/545,058 filed Apr. 7, 2000 and U.S. Ser. No. 09/618,945 filed Jul. 19, 2000, which are all incorporated herein by reference.

FIELD OF THE INVENTION

The present invention relates to semiconductor devices, and in particular, to semiconductor devices having an organic low dielectric constant material and processes for the manufacture thereof.

BACKGROUND OF THE INVENTION

In an effort to increase the performance and speed of semiconductor devices, semiconductor device manufacturers have sought to reduce the linewidth and spacing of interconnects while minimizing the transmission losses and capacitative coupling of the interconnects. One way to diminish power consumption and capacitative coupling is by decreasing the dielectric constant (also referred to as "k") of the insulating material, or dielectric, that separates the interconnects. Insulator materials having low dielectric constants are especially desirable, because they typically allow faster signal propagation, reduce capacitive effects and cross talk between conductor lines, and lower voltages required to drive integrated circuits.

Since air has a dielectric constant of 1.0, a major goal is to reduce the dielectric constant of insulator materials down to a theoretical limit of 1.0, and several methods are known in the art for reducing the dielectric constant of insulating materials. These techniques include adding elements such as fluorine to the composition to reduce the dielectric constant of the bulk material. Other methods to reduce k include use of alternative dielectric material matrices.

Therefore, as interconnect linewidths decrease, concomitant decreases in the dielectric constant of the insulating material are required to achieve the improved performance and speed desired of future semiconductor devices. For example, devices having interconnect linewidths of 0.13 or 0.10 micron and below seek an insulating material having a dielectric constant (k)<3.

Currently silicon dioxide ($SiO_2$) and modified versions of $SiO_2$, such as fluorinated silicon dioxide or fluorinated silicon glass (hereinafter FSG) are used. These oxides, which have a dielectric constant ranging from about 3.5–4.0, are commonly used as the dielectric in semiconductor devices. While $SiO_2$ and FSG have the mechanical and thermal stability needed to withstand the thermal cycling and processing steps of semiconductor device manufacturing, materials having a lower dielectric constant are desired in the industry.

Methods used to deposit dielectric materials maybe divided into two categories: spin-on deposition (hereinafter SOD) and chemical vapor deposition (hereinafter CVD). Several efforts to develop lower dielectric constant materials include altering the chemical composition (organic, inorganic, blend of organic/inorganic) or changing the dielectric matrix (porous, non-porous). Table I summarizes the development of several materials having dielectric constants ranging from 2.0 to 3.5. (PE=plasma enhanced; HDP=high-density plasma) However, these dielectric materials and matrices disclosed in the literature, patent applications or patents shown in Table 1 fail to exhibit many of the combined physical and chemical properties desirable and even necessary for efficient dielectric materials, such as mechanical stability, thermal stability, high glass transition temperature, or appropriate hardness, while at the same time still being able to be solvated and spun on to a substrate, wafer or other surface. Therefore, it may be useful to investigate other compounds and materials that may be useful as dielectric materials and layers, even though these compounds or materials may not be currently contemplated as dielectric materials in their present form.

TABLE I

| MATERIAL | DEPOSITION METHOD | K | REFERENCE |
|---|---|---|---|
| Fluorinated silicon oxide (SiOF) | PE-CVD; HDP-CVD | 3.3–3.5 | U.S. Pat. No. 6,278,174 |
| Hydrogen Silsesquioxane (hereinafter HSQ) | SOD | 2.0–2.5 | U.S. Pat. Nos. 4,756,977; 5,370,903; and 5,486,564; International Patent Publication WO 00/40637; E. S. Moyer et al., "Ultra Low k Silsesquioxane Based Resins", Concepts and Needs for Low Dielectric Constant <0.15 μm Interconnect Materials: Now and the Next Millennium, Sponsored by the American Chemical Society, pages 128–146 (Nov. 14–17, 1999) |
| Methyl Silsesquioxane (hereinafter MSQ) | SOD | 2.4–2.7 | U.S. Pat. No. 6,143,855 |
| Polyorganosilicon | SOD | 2.5–2.6 | U.S. Pat. No. 6,225,238 |
| Fluorinated Amorphous Carbon (a-C:F) | HDP-CVD | 2.3 | U.S. Pat. No. 5,900,290 |
| Benzocyclobutene (hereinafter BCB) | SOD | 2.4–2.7 | U.S. Pat. No. 5,225,586 |
| Polyarylene Ether (hereinafter PAE) | SOD | 2.4 | U.S. Pat. Nos. 5,986,045, 5,874,516, and 5,658,994 |
| Parylene (N and F) | CVD | 2.4 (AF4) | U.S. Pat. No. 5,268,202 |
| Polyphenylenes | SOD | 2.6 | U.S. Pat. Nos. 5,965,679 and 6,288,188B1; and Waeterloos et al., "Integration Feasibility of Porous SiLK Semiconductor Dielectric". Proc. Of the 2001 International Interconnect Tech. Conf., pp. 253–254 (2001). |

Reichert and Mathias describe compounds and monomers that comprise adamantane molecules, which are in the class of cage-based molecules and are taught to be useful as diamond substitutes. (Polym, Prepr. (Am. Chem. Soc., Div. Polym. Chem.), 1993, Vol. 34(1), pp. 495–6; Polym, Prepr. (Am. Chem. Soc., Div. Polym. Chem.), 1992, Vol. 33 (2), pp. 144–5; Chem. Mater., 1993, Vol. 5 (1), pp. 4–5; Macromolecules, 1994, Vol. 27 (24), pp. 7030–7034; Macromolecules, 1994, Vol. 27 (24), pp. 7015–7023; Polym, Prepr. (Am. Chem. Soc., Div. Polym. Chem.), 1995, Vol. 36 (1), pp. 741–742; 205$^{th}$ ACS National Meeting, Conference Program, 1993, pp. 312; Macromolecules, 1994, Vol. 27 (24), pp. 7024–9; Macromolecules, 1992, Vol. 25 (9), pp. 2294–306; Macromolecules, 1991, Vol. 24 (18), pp. 5232–3; Veronica R. Reichert, PhD Dissertation, 1994, Vol. 55–06B; ACS Symp. Ser.: Step-Growth Polymers for High-Performance Materials, 1996, Vol. 624, pp. 197–207; Macromolecules, 2000, Vol. 33 (10), pp. 3855–3859; Polym, Prepr. (Am. Chem. Soc., Div. Polym. Chem.), 1999, Vol. 40 (2), pp. 620–621; Polym, Prepr. (Am. Chem. Soc., Div. Polym. Chem.), 1999, Vol. 40 (2), pp. 577–78; Macromolecules, 1997, Vol. 30 (19), pp. 5970–5975; J. Polym. Sci, Part A: Polymer Chemistry, 1997, Vol. 35 (9), pp. 1743–1751; Polym, Prepr. (Am. Chem. Soc., Div. Polym. Chem.), 1996, Vol. 37 (2), pp. 243–244; Polym, Prepr. (Am. Chem. Soc., Div. Polym. Chem.), 1996, Vol. 37 (1), pp. 551–552; J. Polym. Sci., Part A: Polymer Chemistry, 1996, Vol. 34 (3), pp. 397–402; Polym, Prepr. (Am. Chem. Soc., Div. Polym. Chem.), 1995, Vol. 36 (2), pp. 140–141; Polym, Prepr. (Am. Chem. Soc., Div. Polym. Chem.), 1992, Vol. 33 (2), pp. 146–147; J. Appl. Polym. Sci., 1998, Vol. 68 (3), pp. 475–482). The adamantane-based compounds and monomers described by Reichert and Mathias are preferably used to form polymers with adamantane molecules at the core of a thermoset. The compounds disclosed by Reichert and Mathias in their studies, however, comprise only one isomer of the adamantane-based compound by design choice. Structure A shows this symmetrical para isomer 1,3,5,7-tetrakis (4-phenylethynylphenyl)adamantane:

Structure A

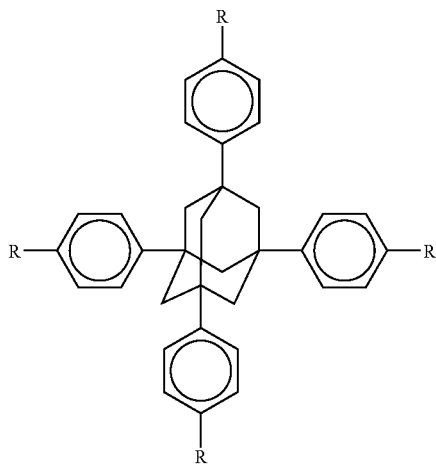

In other words, Reichert and Mathias in their individual and joint work contemplate a useful polymer comprising only one isomer form of the target adamantane-based monomer. A significant problem exists, however, when forming polymers with the single isomer form (symmetrical "all-para" isomer) 1,3,5,7-tetrakis[(4'-phenylethynyl)phenyl]adamantane of the adamantane-based monomer. According to the Reichert dissertation (supra) and Macromolecules, vol. 27, (pp. 7015–7034) (supra), the symmetrical all-para isomer 1,3,5,7-tetrakis[(4'-phenylethynyl)phenyl]adamantane "was found to be soluble enough in chloroform that a $^1$H NMR spectrum could be obtained. However, acquisition times were found to be impractical for obtaining a solution $^{13}$C NMR spectrum." Thus, the Reichert symmetrical "all-para" isomer 1,3,5,7-tetrakis[(4'-phenylethynyl)phenyl]adamantane would not be useful in any application requiring solubility or solvent-based processing, such as flow coating, spin coating, or dip coating.

Although various methods are known in the art to lower the dielectric constant of a material, all, or almost all of them have disadvantages. Thus, there is still a need in the semiconductor industry to a) provide improved compositions and methods to lower the dielectric constant of dielectric layers; b) provide dielectric materials with improved mechanical properties, such as thermal stability, glass transition temperature ($T_g$) and hardness; and c) produce thermosetting compounds and dielectric materials that are capable of being solvated and spun-on to a wafer or layered material.

SUMMARY OF THE INVENTION

Contrary to the Reichert results (which showed a single all "para" phenylethynylphenyl cage-based isomer is insoluble), we have discovered that a novel cage-based isomer mixture is soluble in most organic solvents. As a result of this discovery, this novel cage-based isomer mixture is useful in electronic materials applications wherein the material is dissolved and spun onto a substrate. Further, a process is described herein for converting the Reichert et al. mixture into the present novel cage-based isomer mixture.

Thus, the present invention is generally directed to low dielectric polymers that comprise at least one cage-based molecule or compound and to methods of producing these low dielectric constant polymers, dielectric materials and layers, and electronic components. In one aspect of the present invention, an isomeric mixture of thermosetting monomers, wherein the monomers have a core cage structure and a plurality of arms, is provided, and the isomeric mixture of thermosetting monomers is polymerized, wherein the polymerization process comprises a reaction of an ethynyl group that is located in at least one arm of the monomer.

In a related aspect of the inventive subject matter, the core structure is a cage compound, and preferred arms are aryl, branched aryl or arylene ether. It is also preferred that where the core structure is a cage compound, at least one of the arms has an ethynyl group. Where the core structure is an aryl compound, it is preferred that all of the arms have an ethynyl group. Especially contemplated core structures include adamantane, diamantane, a phenyl, and a sexiphenylene, and especially contemplated arms include a phenylethynylphenyl, a phenylethynylphenylethynylphenyl, a phenylethnylphenylphenyl, and a phenylethynylphenylphenyl ether.

In another aspect of the inventive subject matter the cage structure preferably comprises a substituted or unsubstituted adamantane, or substituted or unsubstituted diamantane, wherein the adamantane or diamantane may be a part of the backbone as a pendent group or such that the cage structure has a tetrahedral or polyhedral configuration.

In another aspect of the inventive subject matter, the polymerization of the isomeric mixture of the thermosetting monomers includes a reaction on more than one ethynyl group of at least one monomer, preferably on three ethynyl groups located on three arms, and more preferably on all ethynyl groups located on all arms. In particularly preferred aspects of the inventive subject matter, the polymerization reaction takes place without participation of an additional molecule and preferably comprises a cycloaddition reaction.

In yet another aspect of the inventive subject matter, spin-on low dielectric constant materials are formed having a first polymer backbone with an aromatic moiety and a first reactive group, and a second polymer backbone with an aromatic moiety and a second reactive group, wherein the first and second polymer backbone are crosslinked via the first and second reactive groups in a crosslinkding reaction preferably without an additional crosslinker, and wherein a cage structure having at least 10 atoms is covalently bound to at least one of the first and second backbones.

In yet another aspect of the inventive subject matter first and second backbone are identical, preferably comprise a phenyl group, more preferably comprise a poly(arylene ether), and most preferably comprise a substituted resorcinol, a substituted tolane, or a substituted phenol as aromatic moiety. In other preferred aspects, the first and second reactive groups are non-identical and comprise an ethynyl moiety or a tetracyclone moiety, and the crosslinking reaction is a cycloaddition reaction.

While it is generally contemplated that isomers of the thermosetting monomer are incorporated in a backbone of a polymer, other positions including the termini and side chains of the polymer are also appropriate. Preferred polymers include poly(arylene ethers) and polymers comprising, or consisting of contemplated thermosetting monomers. Various objects, features, aspects and advantages of the present invention will become more apparent from the following detailed description of preferred embodiments of the invention, along with the accompanying drawing.

BRIEF DESCRIPTION OF THE DRAWING

Table 1 shows some of the representative teachings on low dielectric materials.

FIGS. 2A–2D are exemplary structures for thermosetting monomers comprising sexi-phenylene.

DETAILED DESCRIPTION

As used herein, the term "low dielectric constant polymer" refers to an organic, organometallic, or inorganic polymer with a dielectric constant of approximately 3.0, or lower. As also used herein, the term "backbone" refers to a contiguous chain of atoms or moieties forming a polymeric strand that are covalently bound such that removal of any of the atoms or moiety would result in interruption of the chain.

As further used herein, the term "reactive group" refers to any atom, functionality, or group having sufficient reactivity to form at least one covalent bond with another reactive group in a chemical reaction. The chemical reaction may take place between two identical, or non-identical reactive groups, which maybe located on the same or on two separate backbones. It is also contemplated that the reactive groups may react with one or more than one secondary or exogenous crosslinking molecules to crosslink the first and second backbones. Although crosslinking without exogenous crosslinkers presents various advantages, including reducing the overall number of reactive groups in the polymer, and reducing the number of required reaction steps, crosslinking without exogenous crosslinkers has also a few detriments. For example, the amount of crosslinking functionalities can typically be no more adjusted. On the other hand, employing exogenous crosslinkers may be advantageous when the polymerization reaction and crosslinking reaction are chemically incompatible.

As still further used herein, the phrases "cage structure", "cage molecule", and "cage compound" are intended to be used interchangeably and refer to a molecule having at least eight atoms arranged such that at least one bridge covalently connects two or more atoms of a ring system. In other words, a cage structure, cage molecule or cage compound comprises a plurality of rings formed by covalently bound atoms, wherein the structure, molecule or compound defines a volume, such that a point located within the volume cannot leave the volume without passing through the ring. The bridge and/or the ring system may comprise one or more heteroatoms, and may contain aromatic, partially saturated, or unsaturated groups. Further contemplated cage structures include fullerenes, and crown ethers having at least one bridge. For example, an adamantane or diamantane is considered a cage structure, while a naphthalene or an aromatic spirocompound are not considered a cage structure under the scope of this definition, because a naphthalene or an aromatic spirocompound do not have one, or more than one bridge.

In a method of producing a low dielectric constant polymer, an isomeric mixture of a thermosetting monomer is provided, wherein the monomer has a general structure shown in Structure 1:

Figure 1A:
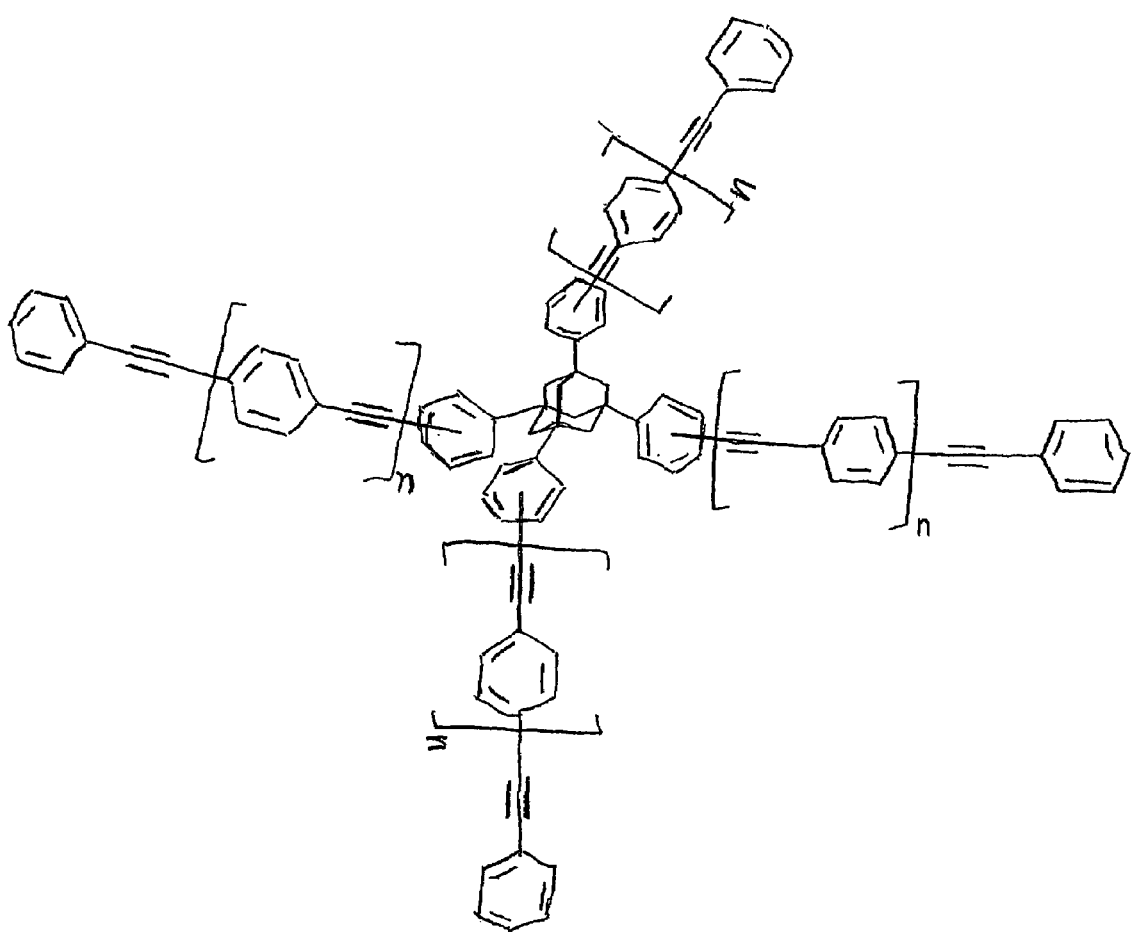
FIGS. 1A–1C are contemplated structures for thermosetting monomers.
Figure 1B:
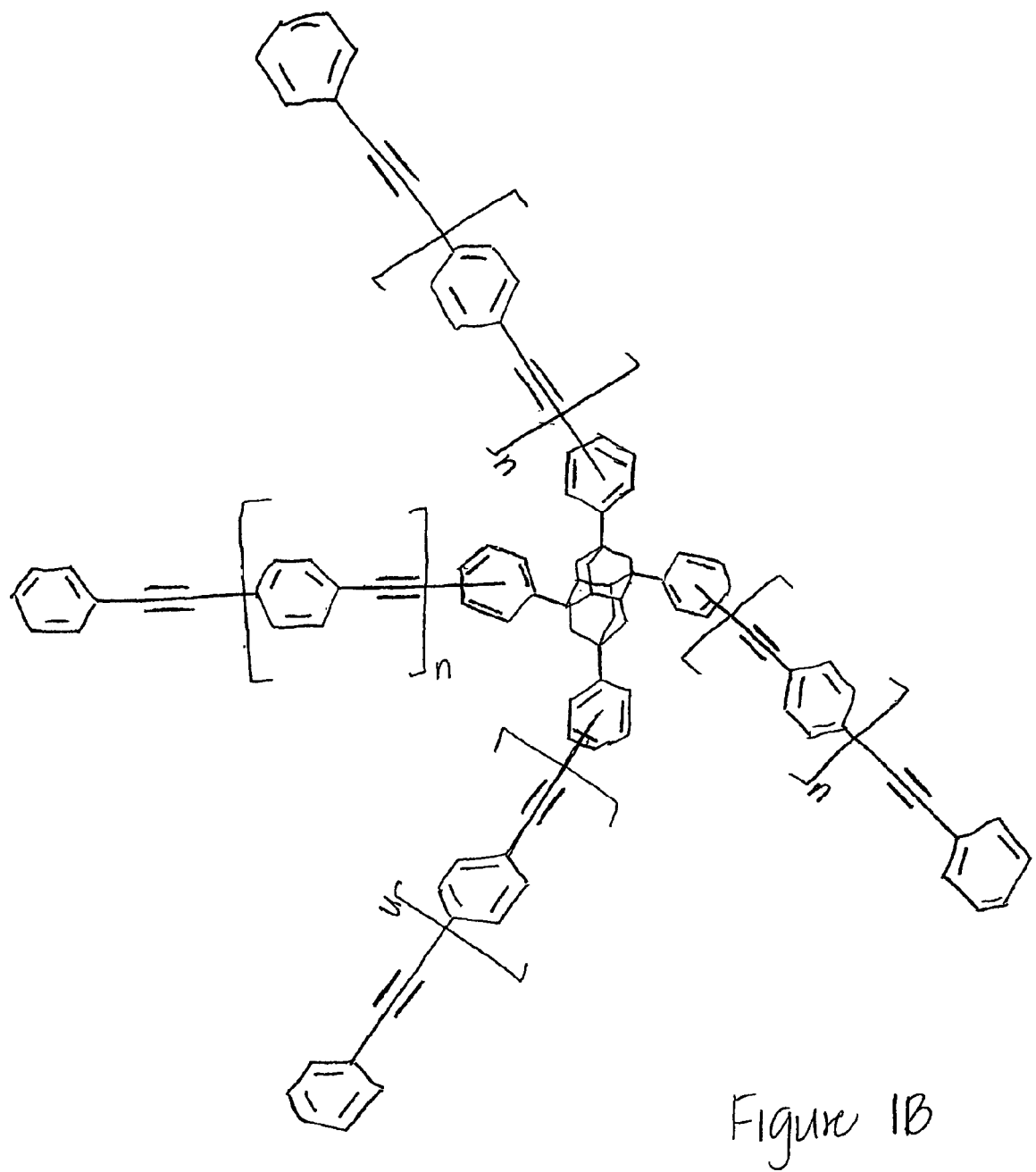
Figure 1C:
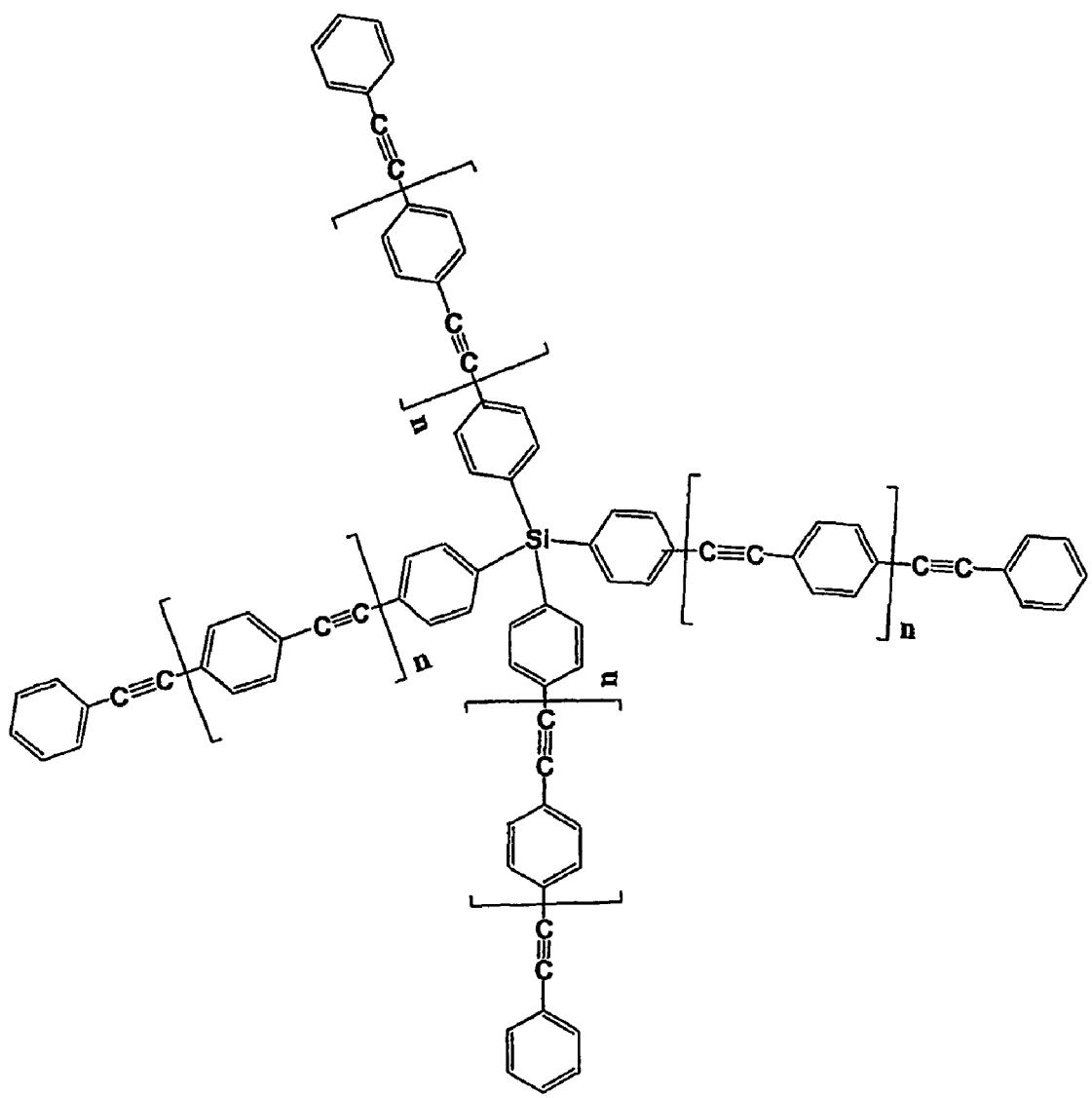

(Structure 1)

wherein Y is selected from a cage compound and a silicon atom, and $R_1$, $R_2$, $R_3$, and $R_4$ are independently selected from an aryl, a branched aryl, and an arylene ether, and wherein at least one of the aryl, the branched aryl, and the arylene ether has an ethynyl group. In a further step, the thermosetting monomer mixture is polymerized thereby forming the low dielectric constant polymer, wherein the polymerization reaction comprises a chemical reaction of the at least one ethynyl group. As used herein, the term "aryl" without further specification means aryl of any type, which may include, for example a branched aryl, or an arylene ether. Exemplary structures of thermosetting monomers that include an adamantane, a diamantane, and a silicon atom are shown in FIGS. 1A, 1B, and 1C, respectively, wherein n is an integer between zero and five, or more.

In another method of producing a low dielectric constant polymer, a thermosetting monomer is provided having a general structure as shown in Structure 2:

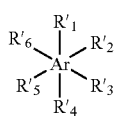

(Structure 2)

wherein Ar is an aryl, and $R'_1$–$R'_6$ are independently selected from an aryl, a branched aryl, an arylene ether and nothing (no substituent at the particular location), and wherein each of the aryl, the branched aryl, and the arylene ether have at least one ethynyl group. In a subsequent step, the thermosetting monomer is polymerized thereby forming a low dielectric constant polymer, wherein polymerization reaction comprises a chemical reaction of the at least one ethynyl group. Exemplary structures of thermosetting monomers that include a tetra-, and a hexasubstituted sexiphenylene are shown in FIGS. 2A–2B and 2C–2D, respectively.

Figure 2B:
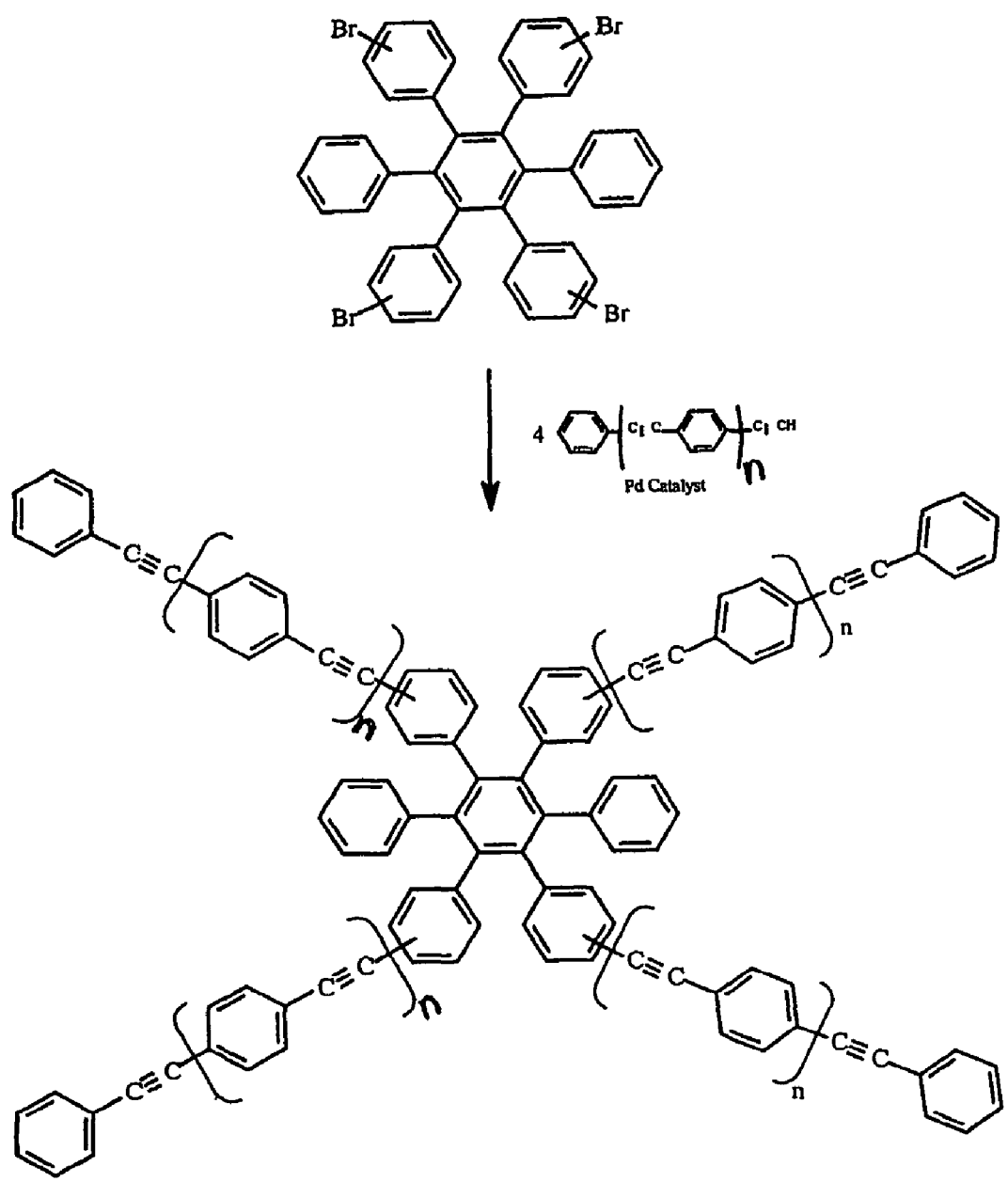
Figure 2D:
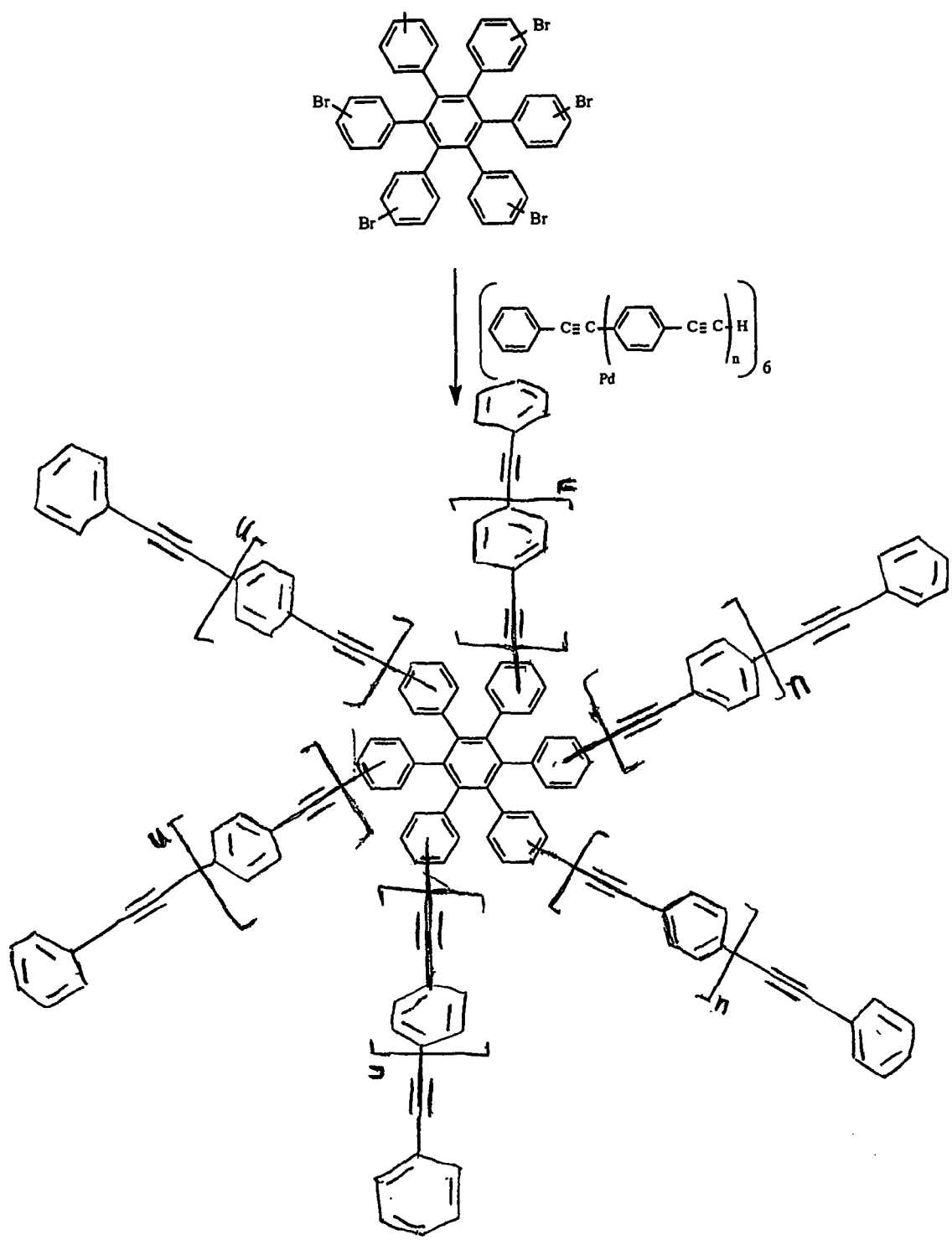
Figure 3A:
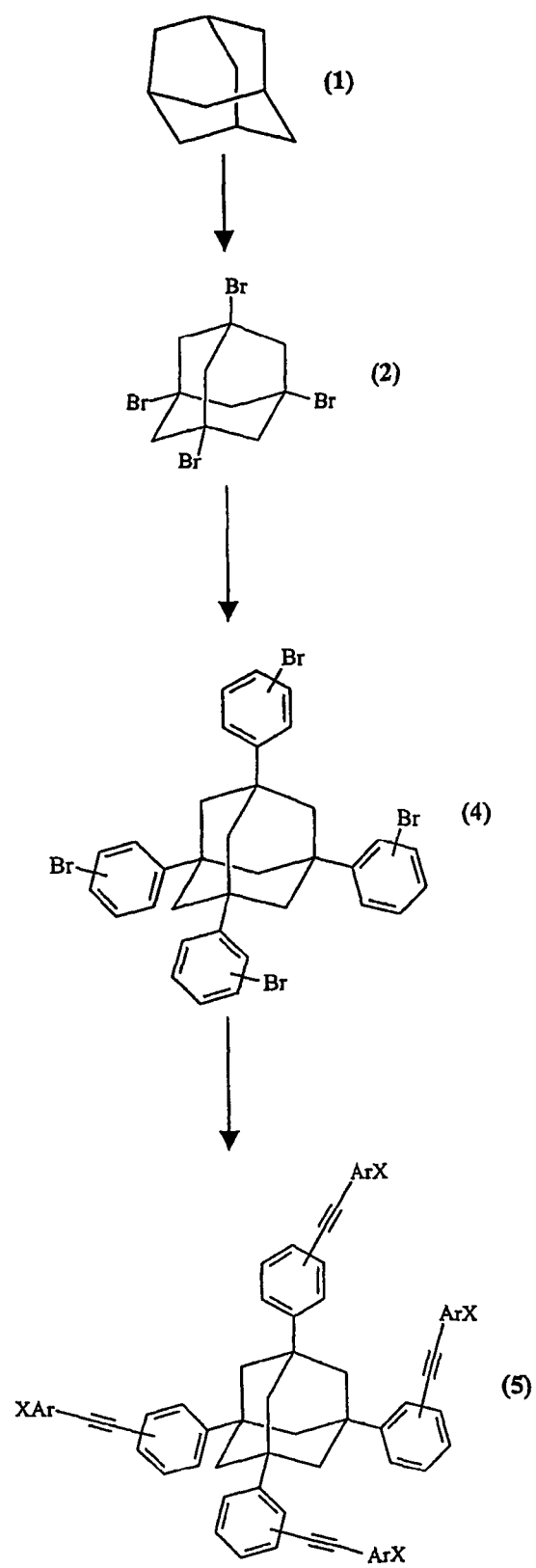
FIGS. 3A–3C are contemplated synthetic schemes for thermosetting.
Figure 3B:
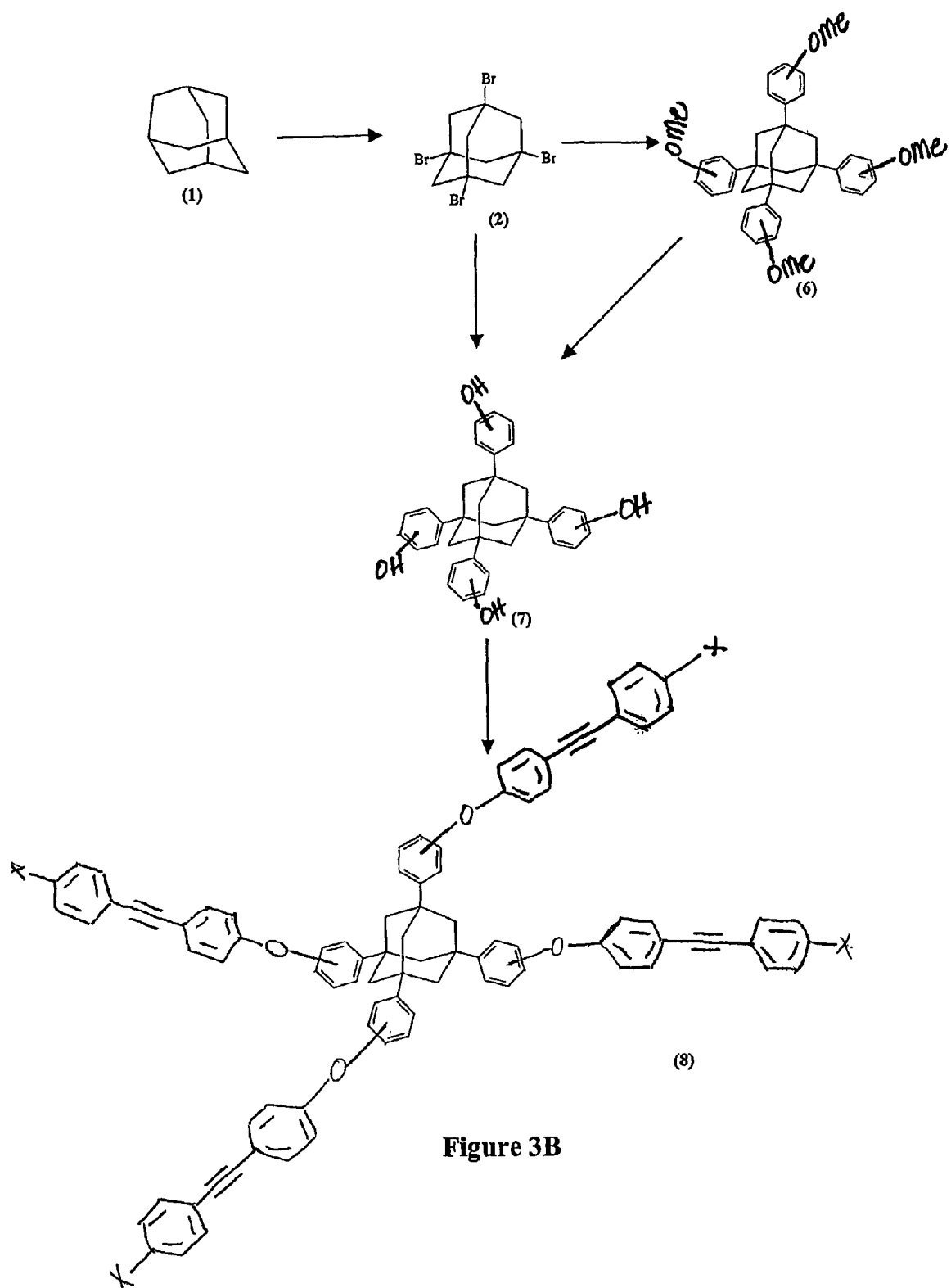
Figure 3C:
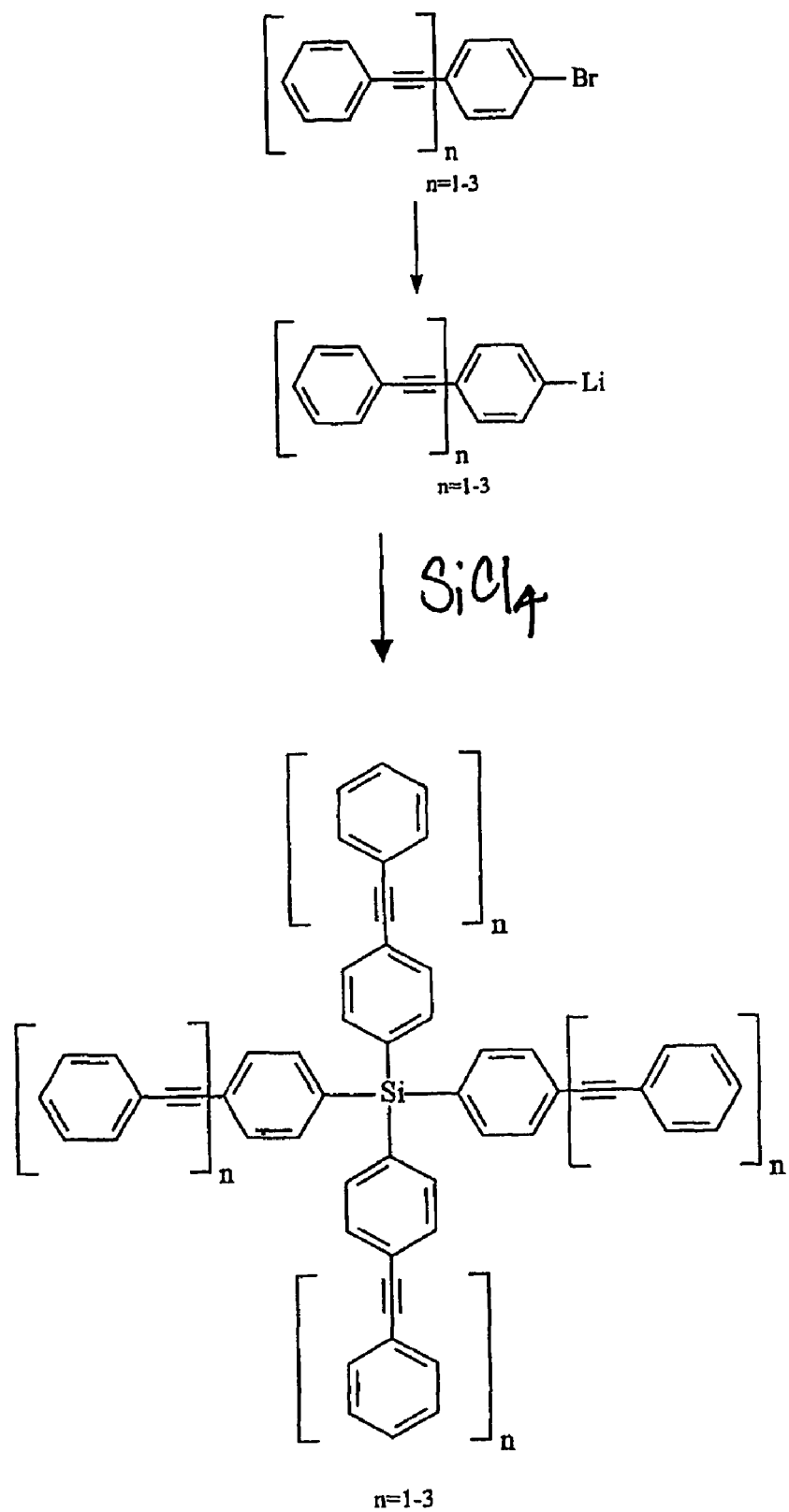

Thermosetting monomers, as generally shown in Structures 1 and 2, may be provided by various synthetic routes, and exemplary synthetic strategies for Structures 1 and 2 are shown in FIGS. 3A–3C. FIG. 3A and Example 5 depicts and describes a preferred synthetic route for the generation of contemplated thermosetting monomers with an adamantane as a cage compound, in which a bromoarene is phenylethynylated in a palladium catalyzed Heck reaction. First, adamantane (1) is brominated to 1,3,5,7-tetrabromoadamantane (TBA) (2) following a procedure previously described (J. Org. Chem. 45, 5405–5408 (1980) by Sollot, G. P. and Gilbert, E. E.). TBA is reacted with phenyl bromide to yield 1,3,5,7-tetra(3/4-bromophenyl)adamantane (TBPA) (4) as described in Macromolecules, 27, 7015–7022 (1990) by Reichert, V. R, and Mathias L. J., and TBPA is subsequently reacted with a substituted ethynylaryl in a palladium catalyzed Heck reaction following standard reaction procedures to yield tetra(arylethynyl-)phenyladamantane (5). Example 5 goes on to show the differences between the Reichert work and compound described in the Background Section and the contemplated compounds of the present invention. The palladium-catalyzed Heck reaction may also be utilized for the synthesis of a thermosetting monomer with a sexiphenylene as the aromatic portion as shown in FIGS. 2A–2D, in which a tetrabromosexiphenylene and a hexabromosexiphenylene, respectively, is reacted with an ethynylaryl compound to yield the desired corresponding thermosetting monomer.

Example 5 also shows another contemplated embodiment of producing a low dielectric constant polymer, which comprises the steps of: (a) providing a chemical reactant having the structure:

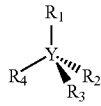

wherein Y is selected from a cage compound, and $R_1$, $R_2$, $R_3$, and $R_4$ are independently reactive groups, such as bromine, fluorine, ethynyl groups, along with those groups already defined herein; (b) converting the chemical reactant to a thermosetting monomer intermediate; (c) subjecting the thermosetting monomer intermediate to a fresh reagent solution and a fresh catalyst to produce a thermosetting monomer, wherein the catalyst comprises $AlBr_3$ or $AlCl_3$; and (d) polymerizing the thermosetting monomer thereby forming the low dielectric constant polymer, wherein polymerizing comprises a chemical reaction of the reactive group.

Alternatively, TBA can be converted to a hydroxyarylated adamantane, which is subsequently transformed into a thermosetting monomer in a nucleophilic aromatic substitution reaction. In FIG. 3B, TBA (2) is generated from adamantane (1) as previously described, and further reacted in an electrophilic tetrasubstitution with phenol to yield 1,3,5,7-tetrakis(3/4-hydroxyphenyl)adamantane (THPA) (2). Alternatively, TBA can also be reacted with anisole to give 1,3,5,7-tetrakis(3'/4'-methoxyphenyl)adamantane (6), which can further be reacted with $BBr_3$ to yield THPA (7). THPA can then be reacted in various nucleophilic aromatic substitution reactions with activated fluoroaromatics in the presence of potassium carbonate employing standard procedures (e.g., Engineering Plastics—A Handbook of Polyarylethers by R. J. Cotter, Gordon and Breach Publishers, ISBN 2-88449-112-0) to produce the desired thermosetting monomers, or THPA may be reacted with 4-halo-4'-fluorotolane (with halo=Br or I) in a standard aromatic substitution reaction (e.g., Engineering Plastics, supra) to yield 1,3,5,7-tetrakis{3'/4'-[4"-(halophenylethynyl)phenoxy]phenyl}adamantane (8). In further alternative reactions, various alternative reactants may also be utilized to generate the thermo setting monomers. Similarly, the nucleophilic aromatic substitution reaction may also be utilized in a synthesis of a thermosetting monomer with a sexiphenylene as the aromatic portion as depicted in FIG. 2D, in which sexiphenylene is reacted with 4-fluorotolane to produce a thermosetting monomer. Alternatively, phloroglucinol may be reacted in a standard aromatic substitution reaction with 4-[4'-(fluorophenylethynyl)phenylethynyl]benzene to yield 1,3,5-tris{4'-[4"-(phenylethynyl)phenylethynyl]phenoxy}benzene.

Where the cage compound is a silicon atom, an exemplary preferred synthetic scheme is depicted in FIG. 3C, in which bromo(phenylethynyl)aromatic arms (9) are converted into the corresponding (phenylethynyl)aryl lithium arms (10), which are subsequently reacted with silicon tetrachloride to yield the desired star shaped thermosetting monomer with a silicon atom as a cage compound.

Although it is preferred that the cage compound is a silicon atom, an adamantane or diamantane, in alternative aspects of the inventive subject matter, various cage compounds other than an adamantane or diamantane are also contemplated. It should be especially appreciated that the molecular size and configuration of the cage compound in combination with the overall length of the arms $R_1$–$R_4$ or $R'_1$–$R'_6$ will determine several of the physical and mechanical properties and the size of voids, if voids are desirable and suitable, in the final low dielectric constant polymer (by steric effect). Therefore, where relatively small cage compounds are desirable, substituted and derivatized adamantanes, diamantanes, and relatively small, bridged cyclic aliphatic and aromatic compounds (with typically less than 15 atoms) are contemplated. In contrast, in cases where larger cage compounds are desirable, larger bridged cyclic aliphatic and aromatic compounds (with typically more than 15 atoms) and fullerenes are contemplated.

Contemplated cage compounds need not necessarily be limited to being comprised solely of carbon atoms, but may also include heteroatoms such as N, S, O, P, etc. Heteroatoms may advantageously introduce non-tetragonal bond angle configurations, which may in turn enable covalent attachment of arms $R_1-R_4$ or $R'_1-R'_6$ at additional bond angles. With respect to substituents and derivatizations of contemplated cage compounds, it should be recognized that many substituents and derivatizations are appropriate. For example, where the cage compounds are relatively hydrophobic, hydrophilic substituents may be introduced to increase solubility in hydrophilic solvents, or vice versa. Alternatively, in cases where polarity is desired, polar side groups may be added to the cage compound. It is further contemplated that appropriate substituents may also include thermolabile groups, nucleophilic and electrophilic groups. It should also be appreciated that functional groups may be utilized in the cage compound (e.g., to facilitate crosslinking reactions, derivatization reactions, etc.). Where the cage compounds are derivatized, it is especially contemplated that derivatizations include halogenation of the cage compound, and particularly preferred halogens are fluorine and bromine.

Where the thermosetting monomer has an aryl coupled to the arms $R'_1-R'_6$ as shown in Structure 2, it is preferred that the aryl comprises a phenyl group, and it is even more preferred that the aryl is a phenyl group or a sexiphenylene. In alternative aspects of the inventive subject matter, it is contemplated that various aryl compounds other than a phenyl group or a sexiphenylene are also appropriate, including substituted and unsubstituted bi- and polycyclic aromatic compounds. Substituted and unsubstituted bi- and polycyclic aromatic compounds are particularly advantageous, where increased size of the thermosetting monomer is preferred. For example, where it is desirable that alternative aryls extend in one dimension more than in another dimension, naphthalene, phenanthrene, and anthracene are particularly contemplated. In other cases, where it is desirable that alternative aryls extend symmetrically, polycyclic aryls such as a coronene are contemplated. In especially preferred aspects, contemplated bi- and polycyclic aryls have conjugated aromatic systems that may or may not include heteroatoms. With respect to substitutions and derivatizations of contemplated aryls, the same considerations apply as for cage compounds, as discussed herein.

With respect to the arms $R_1-R_4$ and $R'_1-R'_6$, it is preferred that $R_1-R_4$ are individually selected from an aryl, a branched aryl, and an arylene ether, and $R'_1-R'_6$ are individually selected from an aryl, a branched aryl, and an arylene ether, and no substitution. Particularly contemplated aryls for $R_1-R_4$ and $R'_1-R'_6$ include aryls having a phenylethynylphenyl, a phenylethynylphenylethynylphenyl, and a phenylethynylphenylphenyl moiety. Especially preferred arylene ethers include phenylethynylphenylphenyl ether.

In alternative aspects of the inventive subject matter, appropriate arms of the thermosetting monomer isomers need not be limited to an aryl, a branched aryl, and an arylene ether, so long as alternative arms $R_1-R_4$ and $R'_1-R'_6$ comprise a reactive group, and so long as the polymerization of the thermosetting monomer comprises a reaction involving the reactive group. For example, contemplated arms may be relatively short with no more than six atoms, which may or may not be carbon atoms. Such short arms may be especially advantageous where voids or pores are desirable to add to the final product or material and the size of voids needs to be relatively small. In contrast, where especially long arms are preferred, the arms may comprise a oligomer or polymer with 7–40, and more atoms. These long arms can be advantageous to design in material stability, thermal stability or even porosity, as compared to the smaller arms. Furthermore, the length as well as the chemical composition of the arms covalently coupled to the contemplated thermosetting monomers may vary within one monomer. For example, a cage compound may have two relatively short arms and two relatively long arms to promote dimensional growth in a particular direction during polymerization. In another example, a cage compound may have two arms chemically distinct from another two arms to promote regioselective derivatization reactions.

While it is preferred that all of the arms in a thermosetting monomer have at least one reactive group, in alternative aspects less than all of the arms need to have a reactive group. For example, a cage compound may have four arms, and only three or two of the arms carry a reactive group. Alternatively, an aryl in a thermosetting monomer may have three arms wherein only two or one arm has a reactive group. It is generally contemplated that the number of reactive groups in each of the arms $R_1-R_4$ and $R'_1-R'_6$ may vary considerably, depending on the chemical nature of the arms and of the qualities of the desired end product. Moreover, reactive groups are contemplated to be positioned in any part of the arm, including the backbone, side chain or terminus of an arm. It should be especially appreciated that the number of reactive groups in the thermosetting monomer may be utilized as a tool to control the degree of crosslinking. For example, where a relatively low degree of crosslinking is desired, contemplated thermosetting monomers may have only one or two reactive groups, which may or may not be located in one arm. On the other hand, where a relatively high degree of crosslinking is required, three or more reactive groups may be included into the monomer. Preferred reactive groups include electrophilic and nucleophilic groups, more preferably groups that may participate in a cycloaddition reaction and a particularly preferred reactive group is an ethynyl group.

In addition to reactive groups in the arms, other groups, including functional groups may also be included into the arms. For example, where addition of particular functionalities (e.g., a thermolabile portion) after the polymerization of the thermosetting monomer into a polymer is desirable, such functionalities may be covalently bound to the functional groups.

The thermosetting monomers, monomer mixtures and isomer mixtures can be polymerized by a large variety of mechanisms, and the actual mechanism of polymerization predominantly depends on the reactive group that participates in the polymerization process. Therefore, contemplated mechanisms include nucleophilic, electrophilic and aromatic substitutions, additions, eliminations, radical polymerization reactions, and cycloaddition reaction, and a particularly preferred polymerization mechanism is a cycloaddition that involves at least one ethynyl group located at least one of the arms. For example, in a thermosetting monomer having arms selected from an aryl, a branched aryl and an arylene ether, in which at least three of the aryl, the branched aryl, and the arylene ether have a single ethynyl group, the polymerization of the monomer, isomer mixtures, or monomer mixture into the polymer may comprise a cycloaddition reaction (i.e. a chemical reaction) of at least three ethynyl groups. In another example, in a thermosetting monomer wherein all of the aryl, the branched aryl, and the arylene ether arms have a single ethynyl group, the polymerization process may comprise a cycloaddition reaction (i.e. a chemical reaction) of all of the ethynyl groups. In other examples, cycloaddition reaction (e.g., a Diels-Alder reaction) may occur between an ethynyl group in at least one arm of the thermosetting monomer and a diene group located in a polymer. It is further contemplated that the polymerization of the thermosetting monomers takes place without participation of an additional molecule (e.g., a crosslinker), preferably as a cycloaddition reaction between reactive groups of thermosetting monomers. However, in alternative aspects of the inventive subject matter, crosslinkers may be utilized to covalently couple a thermosetting monomer to a polymer. Such covalent coupling may thereby either occur between a reactive group and a polymer or a functional group and a polymer.

Depending on the mechanism of polymerization of the thermosetting monomer, reaction conditions may vary considerably. For example, where a monomer is polymerized by a cycloaddition reaction utilizing an ethynyl group of at least one of the arms, heating of the thermosetting monomer to approximately 250° C. or greater for about 45 min is generally sufficient. In contrast, where the monomer is polymerized by a radical reaction, addition of a radical starter may be appropriate. Preferred polymerization methods and techniques are set forth in the examples.

The thermosetting monomer may be located at any point in or on the polymer backbone, including the terminus or as a side chain of the polymer. As used herein, the term "backbone" refers to a contiguous chain of atoms or moieties forming a polymeric strand that are covalently bound such that removal of any of the atoms or moiety would result in interruption of the chain.

Contemplated polymers include a large variety of polymer types such as polyimides, polystyrenes, polyamides, etc. However, it is especially contemplated that the polymer comprises a polyarylene, more preferably a poly(arylene ether). In an even more preferred aspect, the polymer is fabricated at least in part from the thermosetting monomer, and it is particularly contemplated that the polymer is entirely fabricated from isomers of the thermosetting monomer.

Figure 4:
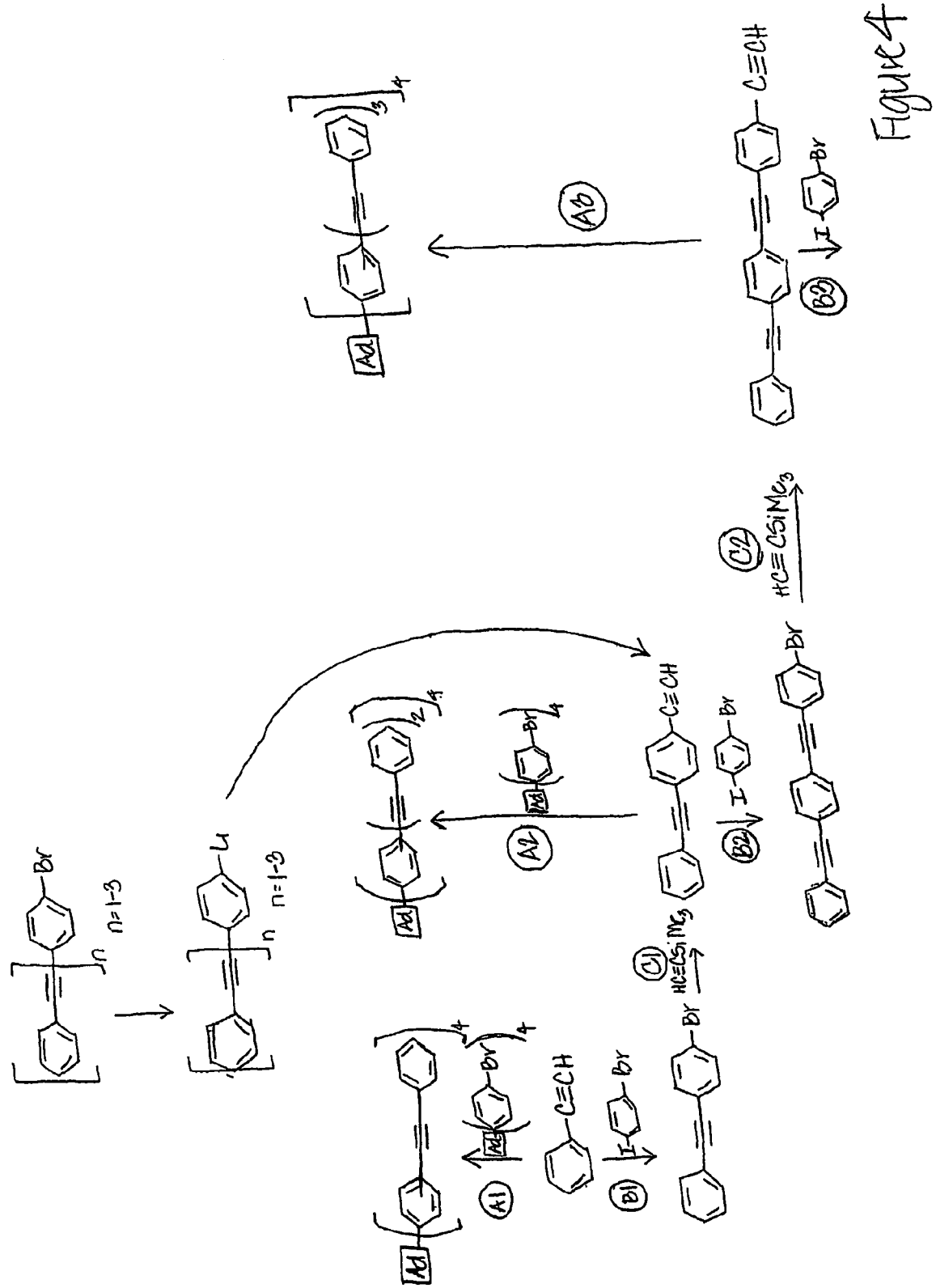
FIG. 4 is a synthetic scheme to produce substituted adamantanes.

In an especially contemplated arm extension strategy depicted in FIG. 4, in which AD represents an adamantane or diamantane group. Phenylacetylene is a starting molecule that is reacted (A1) with TBPA (supra) to yield 1,3,5,7-tetrakis[3'/4'-(phenylethynyl)phenyl]adamantane. Alternatively, phenylacetylene can be converted (B1) to 4-(phenylethynyl)phenylbromide that is subsequently reacted (C1) with trimethylsilylacetylene to form 4-(phenylethynyl)phenylacetylene. TBPA can then be reacted (with phenylethynylphenylacetylene to 1,3,5,7-tetrakis{3'/4'-[4"-(phenylethynyl)phenylethynyl]phenyl}-adarnantane. In a further extension reaction, phenylethynylphenylacetylene is reacted (2) with 1-bromo-4-iodobenzene to form 4-[4'-(phenylethynyl)phenylethynyl]phenylbromide that is further converted (C2) to 4-[4'-(phenylethynyl)phenylethynyl]acetylene. The so formed 4-[4'-(phenylethynyl)phenylethynyl]acetylene may then be reacted (A3) with TBA to yield 1,3,5,7-tetrakis-{3'/4'-[4"-(4'-(phenylethynyl)phenylethynyl)phenylethynyl]phenyl}adamantane.

The thermosetting monomers and isomeric mixtures of the contemplated thermosetting monomers according to the inventive subject matter may be utilized in a dielectric layer of an electronic device, wherein preferred dielectric layers have a dielectric constant of less than 3.0, and preferred electric devices include an integrated circuit. Therefore, a contemplated electrical device may include at least one dielectric layer, wherein the dielectric layer comprises a polymer fabricated from at least one of a thermosetting monomer or isomeric monomer mixture having the structures:

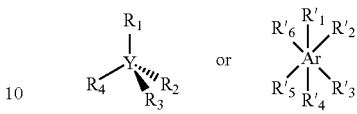

wherein Y is a cage compound or a silicon atom, Ar is preferably an aryl, $R_1$–$R_4$ are independently selected from an aryl, a branched aryl, and an arylene ether, $R'_1$–$R'_6$ are independently selected from an aryl, a branched aryl, and an arylene ether and no substitution, and wherein at least one of the aryl, the branched aryl, and the arylene ether has an ethynyl group.

More specifically, preferred spin-on low dielectric constant materials can be formed comprising a first and second backbone, wherein at least one backbone comprise a poly (arylene ether) with two pendent adamantane groups, respectively, as cage structures as shown in Structures 3A–B (only one repeating unit of the backbone is shown). These low dielectric constant materials generally comprise the following repeating unit:

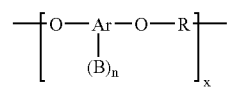

wherein B is a phenyladamantane or phenyldiamantane polymer (where n=1–3) and wherein x=1–$10^3$, R comprises at least one phenyl group, and Ar is a phenyl group. More specifically, it is contemplated that B comprises:

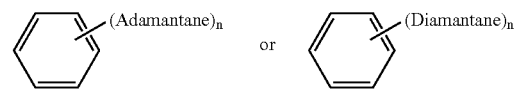

It is further contemplated that R comprises:

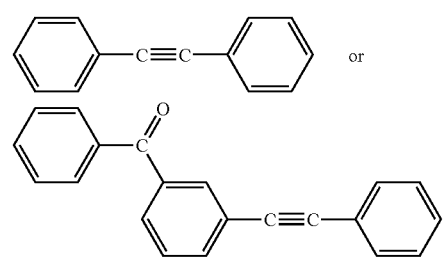

The first and second aromatic moieties comprise a phenyl group, and the first and second reactive groups are an ethynyl and a tetracyclone moiety, respectively, which react in a Diels-Alder reaction to cross-link the backbones. Preferred crosslinking conditions are heating the poly(arylene ether) backbones to a temperature of about 200° C.–250° C.

or greater for approximately 30–180 minutes. Structure 3B can be synthesized as generally outlined in Examples 1–3 below.

Structure 3A

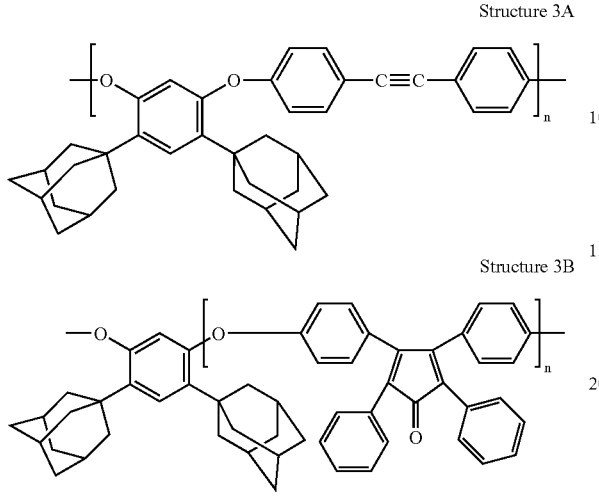

Structure 3B

In alternative embodiments, the backbone need not be restricted to a poly(arylene ether), but may vary greatly depending on the desired physico-chemical properties of the final low dielectric constant material. Consequently, when relatively high $T_g$ is desired, inorganic materials are especially contemplated, including inorganic polymers comprising silicate ($SiO_2$) and/or aluminate ($Al_2O_3$). In cases where flexibility, ease of processing, or low stress/TCE, etc. is required, organic polymers are contemplated. Thus, depending on a particular application, contemplated organic backbones include aromatic polyimides, polyamides, and polyesters.

Figure 5:
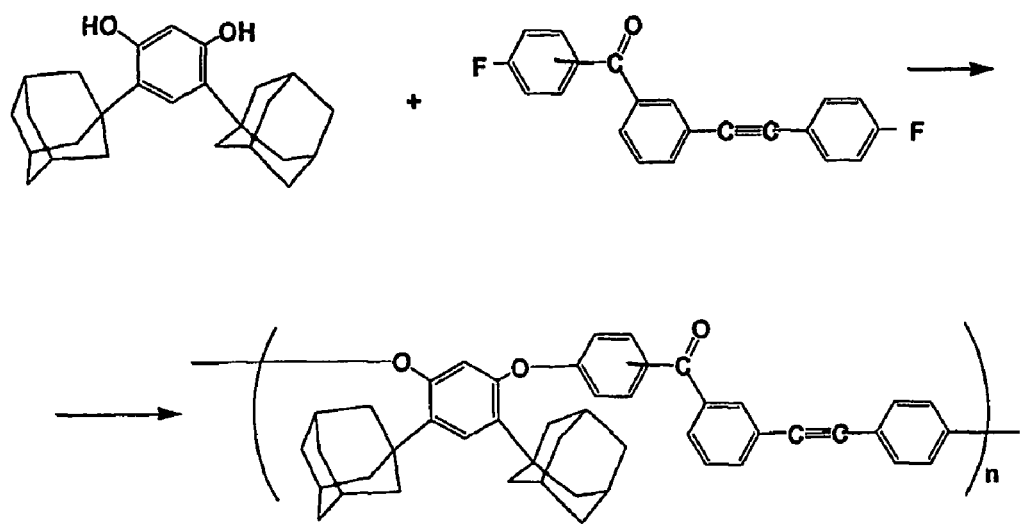
FIG. 5 is a synthetic scheme to produce a low molecular weight polymer with pendent cage structures.
Figure 6:
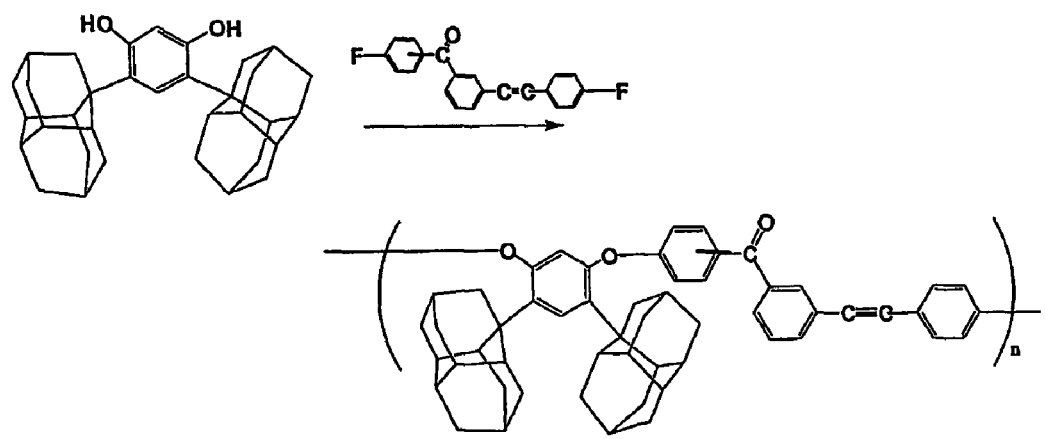
FIG. 6 is a synthetic scheme to produce a low molecular weight polymer with pendent cage structures.

Although preferably built from low molecular weight polymers with a molecular weight of approximately 1000 to 10000, the chain length of the first and second polymeric backbones may vary considerably between five, or less repeating units, to several $10^4$ repeating units, and more. Preferred backbones are synthesized from monomers in an aromatic substitution reaction, and synthetic routes are shown by way of example in FIGS. 5 and 6. It is further contemplated that alternative backbones may also be branched, superbranched, or crosslinked at least in part. Alternatively, the backbones may also be synthesized in-situ from monomers. Appropriate monomers may preferably include aromatic bisphenolic compounds and difluoroaromatic compounds, which may have between 0 and about 20 built-in cage structures.

It is again contemplated that appropriate monomers and isomeric mixtures may have or comprise a tetrahedral structure, which are schematically depicted in Structures 4A–B. In general Structure 4A, a thermosetting monomer has a cage structure G, and at least two of the side chains $R_1$–$R_4$ comprise an aromatic portion and a reactive group, wherein at least one of the reactive groups of a first monomer reacts with at least one of the reactive group of a second monomer to produce a low dielectric constant polymer. In general Structure 4B a cage structure, preferably an adamantane, is coupled to four aromatic portions which may participate in polymerization, and wherein $R_1$–$R_4$ may be identical or different.

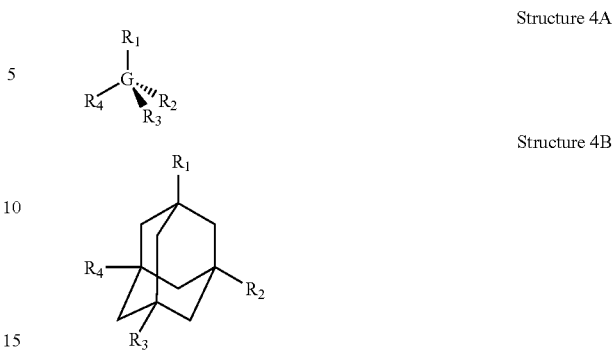

Structure 4A

Structure 4B

Figure 7:
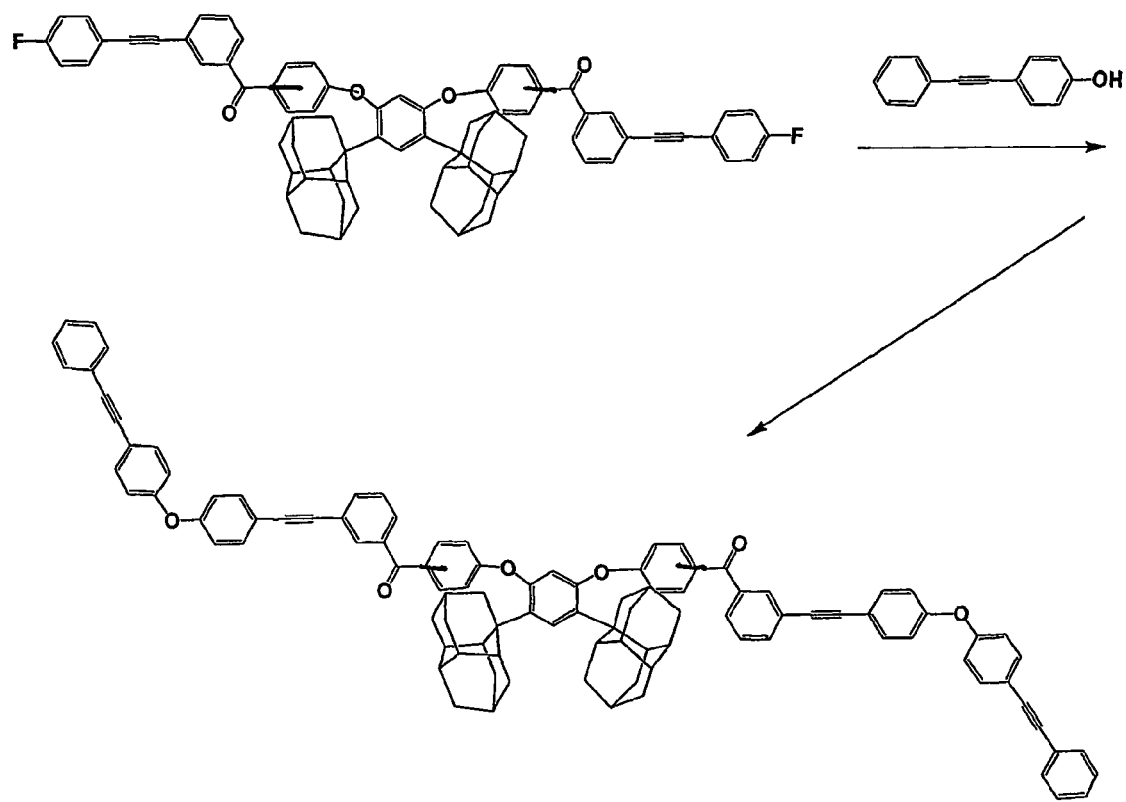
FIG. 7 shows a synthetic scheme to produce thermosetting monomers.

When monomers with tetrahedral structure are used, the cage structure will covalently connect four backbones in a three dimensional configuration. An exemplary monomer with tetrahedral structure and its synthesis is shown in FIG. 7. It should further be appreciated that alternative monomers need not be limited to compounds with a substituted or unsubstituted adamantane as a cage structure, but may also comprise a substituted or unsubstituted diamantane, or fullerene as a cage structure. Contemplated substituents include alkyls, aryls, halogens, and functional groups. For example, an adamantane may be substituted with a —CF3 group, a phenyl group, —COOH, —$NO_2$, or —F, —Cl, or —Br. Consequently, depending on the chemical nature of the cage structure, various numbers other than four aromatic portions may be attached to the cage structure. For example, where a relatively low degree of crosslinking through cage structures is desired, one to three aromatic portions may be attached to the cage structure, wherein the aromatic portions may or may not comprise a reactive group for crosslinking. In cases where higher degrees of crosslinking is preferred, five and more aromatic portions may be attached to a cage structure wherein all or almost all of the aromatic portions carry one or more than one reactive group. Furthermore, it is contemplated that aromatic portions attached to a central cage structure may carry other cage structures, wherein the cage structures may be identical to the central cage structure, or may be entirely different. For example, contemplated monomers may have a fullerene cage structure to provide a relatively high number of aromatic portions, and a diamantane in the aromatic portions. Thus, contemplated cage structures may be covalently bound to a first and second backbone, or to more than two backbones.

With respect to the chemical nature of the aromatic portion, it is contemplated that appropriate aromatic portions comprise a phenyl group, and more preferably a phenyl group and a reactive group. For example, an aromatic portion may comprise a tolane (phenylethynylphenyl) group, or a substituted tolane, wherein substituted tolanes may comprise additional phenyl groups covalently bound to the tolane via carbon-carbon bonds, or carbon-non-carbon atom bonds, including double and ethynyl groups, ether-, keto-, or ester groups.

Also contemplated are monomers that have pendent cage structures, as depicted by way of example in FIG. 7, in which two diamantane groups are utilized as pendent groups. It should be appreciated, however, that pending cage structures are not limited to two diamantane structures. Contemplated alternative cage structures include single and multiple substituted adamantane groups, diamantane groups and fullerenes in any chemically reasonable combination.

Substitutions may be introduced into the cage structures in cases where a particular solubility, oxidative stability, or other physico-chemical properties are desired. Therefore, contemplated substitutions include halogens, alkyl, aryl, and alkenyl groups, but also functional and polar groups including esters, acid groups, nitro and amino groups, and so forth.

It should also be appreciated that the backbones need not be identical. In some aspects of alternative embodiments, two, or more than two chemically distinct backbones may be utilized to fabricate a low dielectric constant material, as long as the alternative low dielectric constant material comprises first and second backbones having an aromatic moiety, a reactive group, and a cage compound covalently bound to the backbone.

With respect to the reactive groups it is contemplated that many reactive groups other than an ethynyl group and a tetracyclone group may be utilized, so long as alternative reactive groups are able to crosslink first and second backbones without an exogenous crosslinker. For example, appropriate reactive groups include benzocyclobutenyl. In another example, a first reactive group may comprise an electrophile, while a second reactive group may comprise a nucleophile. It is further contemplated that the number of reactive groups predominantly depends on (a) the reactivity of the first and second reactive group, (b) the strength of the crosslink between first and second backbone, and (c) the desired degree of crosslinking in the low dielectric material. For example, when the first and second reactive groups are sterically hindered (e.g. an ethynyl group between two derivatized phenyl rings), a relatively high number of reactive groups may be needed to crosslink two backbones to a certain extent. Likewise, a high number of reactive groups may be required to achieve stable crosslinking when relatively weak bonds such as hydrogen bonds or ionic bonds are formed between the reactive groups.

In cases where a reactive group in one backbone is capable of reacting with an identical reactive group in another backbone, only one type of reactive group maybe needed. For example, ethynyl groups located on the same of two different backbones may react in an addition and cycloaddition-type reaction to form crosslinking structures.

It should also be appreciated that the number of reactive groups may influence the ratio of intermolecular to intramolecular crosslinking. For example, a relatively high concentration of reactive groups in first and second backbones at a relatively low concentration of both backbones may favor intramolecular reactions. Similarly, a relatively low concentration of reactive groups in first and second backbones at a relatively high concentration of both backbones may favor inter-molecular reactions. The balance between intra- and intermolecular reactions may also be influenced by the distribution of non-identical reactive groups between the backbones. When an intermolecular reaction is desired, one type of reactive group may be placed on the first backbone, while another type of reactive group may be positioned on the second backbone. Furthermore, additional third and fourth reactive groups may be utilized when sequential crosslinking at different conditions is desired (e.g. two different temperatures).

The reactive groups of preferred backbones react in an addition-type reaction, however, depending on the chemical nature of alternative reactive groups, many other reactions are also contemplated, including nucleophilic and electrophilic substitutions, or eliminations, radical reactions, etc. Further alternative reactions may also include the formation of non-covalent bonds, such as electrostatic bonds, ionic bonds and hydrogen bonds. Thus, crosslinking the first and second backbone may occur via a covalent or non-covalent bond formed between identical or non-identical reactive groups, which may be located on the same or two backbones.

Figure 8A:
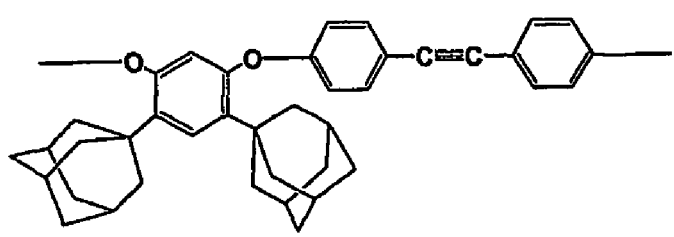
FIGS. 8A–B are structures of various contemplated polymers.
Figure 8B:
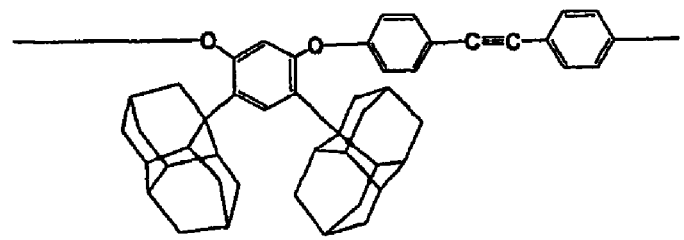

In further aspects of alternative embodiments, the cage structure may comprise structures other than an adamantane, including a diamantane, bridged crown ethers, or fullerenes, as long as alternative cage structures have at least eight atoms. The selection of appropriate cage structures is determined by the desired degree of steric demand of the cage structure. If relatively small cage structures are preferred, a single adamantane, or diamantane group may be sufficient. Contemplated structures of backbones including adamantane and diamantane groups are shown in FIGS. 8A and 8B. Large cage structures may comprise fullerenes. It should also be appreciated that alternative backbones need not be limited to a single type of cage structure. Appropriate backbones may also include two to five cage structures or other molecules and more non-identical cage structures. For example, fullerenes may be added to one or both ends of a polymeric backbone, while diamantane groups are placed in the other parts of the backbone. Further contemplated are derivatized, or multiple cage structures, including oligomerized and polymerized cage structures, where even larger cage structures are desired. The chemical composition of the cage structures need not be limited to carbon atoms, and it should be appreciated that alternative cage structures may have atoms other than carbon atoms (i.e. hetero-atoms), whereby contemplated heteroatoms may include N, O, P, S, B, etc.

Figure 9A:
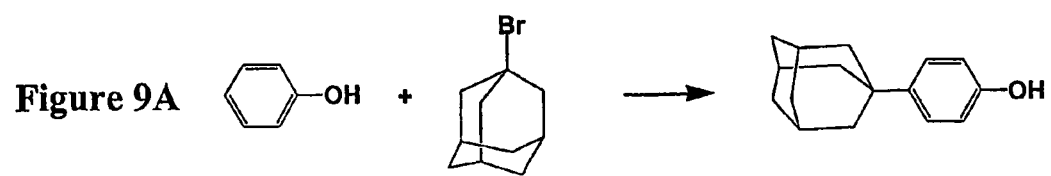
FIGS. 9A–B are synthetic schemes to produce an end-capping molecule with pendent cage structures.
Figure 9B:
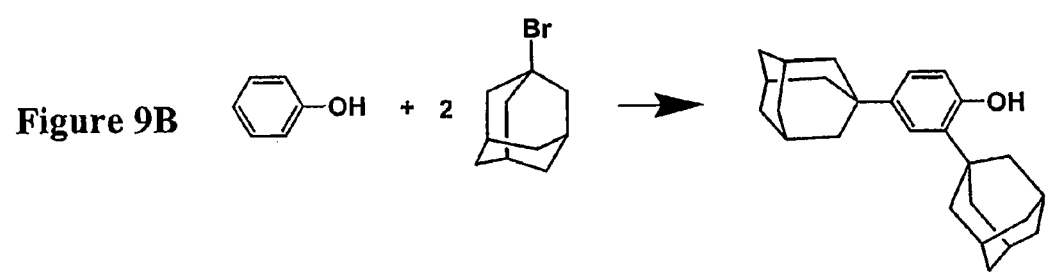

With respect to the position of the cage structure, it is contemplated that the cage structure maybe connected to the backbone in various locations. For example, when it is desirable to mask terminal functional groups in the backbone, or to terminate a polymerization reaction forming a backbone, the cage structure may be utilized as an end-cap. Exemplary structures of end-caps are shown in FIGS. 9A and 9B. In other cases where large amounts of a cage structure are desired, it is contemplated that the cage structures are pendent structures covalently connected to the backbone. The position of the covalent connection may vary, and mainly depends on the chemical make-up of the backbone and the cage structure. Thus, appropriate covalent connections may involve a linker molecule, or a functional group, while other connections may be a single or double bond. When the cage group is a pendent group it is especially contemplated that more than one backbone maybe connected to the cage structure. For example, a single cage structure may connect at least two or three or and more backbones. Alternatively, it is contemplated that the cage group may be an integral part of the backbone.

Figure 10:
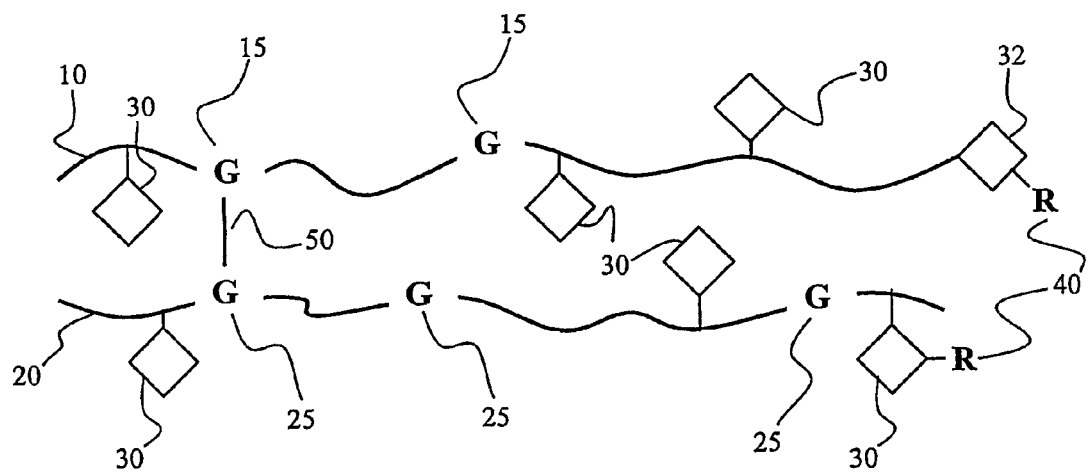
FIG. 10 is schematic structure of a contemplated low dielectric constant material.

Turning now to FIG. 10, an exemplary low dielectric constant material is shown in which a first backbone 10 is crosslinked to a second backbone 20 via a first reactive group 15 and a second reactive group 25, wherein the crosslinking results in a covalent bond 50. Both backbones have at least one aromatic moiety (not shown), respectively. A plurality of pendent cage structures 30 are covalently bound to the first and second backbones, and the first backbone 10 further has a terminal cage group 32. The terminal cage group 32, and at least one of the pendent cage groups 30 carries at least one substituent R (40), wherein substituent 40 may be a halogen, alkyl, or aryl group. Each of the cage structures comprises at least eight (8) atoms.

It is still further contemplated that alternative low dielectric constant material may also comprise additional components. For example, protective agents may be added. In other cases where the dielectric material is placed on a smooth surface, adhesion promoters may be advantageously utilized. In still other cases the addition of detergents or antifoam agents may be desirable.

The monomers, monomer mixtures and polymers described herein can be and in many ways are designed to be solvated or dissolved in any suitable solvent, so long as the resulting solutions can be spin coated or otherwise mechanically layered on to a substrate, a wafer or layered material. Substrates contemplated herein may comprise any desirable substantially solid material. Particularly desirable substrate layers would comprise films, glass, ceramic, plastic, metal or coated metal, or composite material. In preferred embodiments, the substrate comprises a silicon or gallium arsenide die or wafer surface, a packaging surface such as found in a copper, silver, nickel or gold plated leadframe, a copper surface such as found in a circuit board or package interconnect trace, a via-wall or stiffener interface ("copper" includes considerations of bare copper and it's oxides), a polymer-based packaging or board interface such as found in a polyimide-based flex package, lead or other metal alloy solder ball surface, glass and polymers. In more preferred embodiments, the substrate comprises a material common in the packaging and circuit board industries such as silicon, copper, glass, and polymers.

Preferred solutions are designed and contemplated to be spin coated, rolled, dripped or sprayed onto a wafer, a substrate or layered material. Most preferred solutions are designed to be spin coated onto a wafer, a substrate or layered material. Typical solvents are those solvents that are readily available to those in the field of dielectric materials, layered components or electronic components.

Typical solvents are also those solvents that are able to solvate the monomers, isomeric monomer mixtures and polymers. Contemplated solvents include any suitable pure or mixture of organic, organometallic or inorganic molecules that are volatilized at a desired temperature. The solvent may also comprise any suitable pure or mixture of polar and non-polar compounds. In preferred embodiments, the solvent comprises water, ethanol, propanol, acetone, toluene, ethers, cyclohexanone, butyrolactone, methylethylketone, methylisobutylketone, N-methylpyrrolidone, polyethyleneglycolmethylether, mesitylene, and anisole.

The present composition may be used in an all spin-on stacked film as taught by Michael E. Thomas, "Spin-On Stacked Films for Low $k_{eff}$ Dielectrics", *Solid State Technology* (July 2001), incorporated herein in its entirety by reference.

EXAMPLES

Analytical Test Methods:

Dielectric Constant: The dielectric constant was determined by coating a thin film of aluminum on the cured layer and then doing a capacitance-voltage measurement at 1 MHz and calculating the k value based on the layer thickness.

Glass Transition Temperature (Tg): The glass transition temperature of a thin film is determined by measuring the thin film stress as a function of temperature. The thin film stress measurement is performed on a KLA 3220 Flexus. Before the film measurement, the uncoated wafer is annealed at 500° C. for 60 min to avoid any errors due to stress relaxation in the wafer itself. The wafer is then deposited with the material to be tested and processed through all required process steps. The wafer is then placed in the stress gauge, which measures the wafer bow as function of temperature. The instrument can calculate the stress versus temperature graph, provided that the wafer thickness and the film thickness are known. The result is displayed in graphic form. To determine the Tg value, a horizontal tangent line is drawn (a slope value of zero on the stress vs. temperature graph). Tg value is where the graph and the horizontal tangent line intersect.

It should be reported if the Tg was determined after the first temperature cycle or a subsequent cycle where the maximum temperature was used, the measurement process itself may influence Tg.

Shrinkage: Film shrinkage is measured by determining the film thickness before and after the process. Shrinkage is expressed in percent of the original film thickness. Shrinkage is positive if the film thickness decreased. The actual thickness measurements are performed optically using a J. A. Woollam M-88 spectroscopic ellipsometer. A Cauchy model is used to calculate the best fit for Psi and Delta (details on Ellipsometry can be found in e.g. "Spectroscopic Ellipsometry and Reflectometry" by H. G. Thompkins and William A. McGahan).

Refractive Index; The refractive index measurements are performed together with the thickness measurements using a J. A. Woollam M-88 spectroscopic ellipsometer. A Cauchy model is used to calculate the best fit for Psi and Delta. Unless noted otherwise the refractive index is reported at a wavelenth of 633 nm (details on Ellipsometry can be found in e.g. "Spectroscopic Ellipsometry and Reflectometry" by H. G. Thompkins and William A. McGahan).

Example 1

Synthesis of 4,6-bis(adamantyl)resorcinol

Into a 250-mL 3-neck flask, equipped with nitrogen inlet, thermocouple and condenser, were added resorcinol (11.00 g, 100.0 mMol), bromoadmantane (44.02 g, 205.1 mMol) and toluene (150 mL). The mixture was heated to 110° C. and became a clear solution. The reaction was allowed to continue for 48 h, at which time TLC showed that all the resorcinol had disappeared. The solvent was removed and the solid was crystallized from hexanes (150 mL). The disubstituted product was obtained in 66.8% yield (25.26 g) as a white solid. Another 5.10 g product was obtained by silica gel column chromatography of the concentrated mother liquor after the first crop. The total yield of the product was 80.3%. Characterization of the product was by proton NMR, HPLC, FTR and Mass Spectrometry (MS).

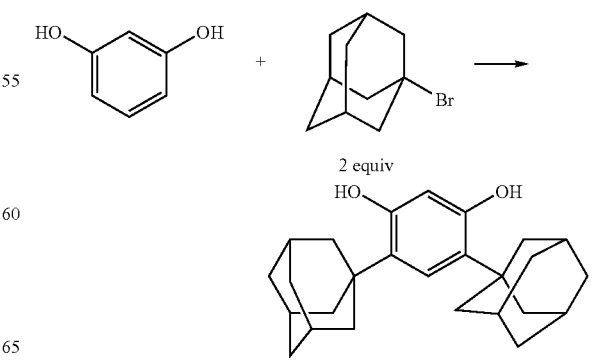

Polymerization of 4,6-bis(adamantyl)resorcinol into a poly(arylene ether) backbone In a 250-mL 3-neck flask, equipped with a nitrogen inlet, thermocouple and Dean-Stark trap, were added bis(adamantyl)resorcinol (7.024 g, 18.57 mMol), FBZT (5.907 g, 18.57 mMol), potassium carbonate (5.203 g, 36.89 mMol) and DMAC (50 mL), toluene (25 mL). The reaction mixture was heated to 135° C. to produce a clear solution. The reaction was continued for 1 h at this temperature and the temperature was raised to 165° C. by removing some of the toluene. The course of polymerization was monitored by GPC. At $M_w$=22,000, the reaction was stopped. Another 50-mL portion of DMAC was added to the reaction flask. The solid was filtered at room temperature, and was extracted with hot dichloromethane (2×150 mL). Methanol (150 mL) was added to the solution to precipitate a white solid, which was isolated by filtration. The yield was 65.8% (8.511 g). The solid was dissolved in THF (150 mL) and methanol (300 mL) was added to the solution slowly. The precipitated white solid was isolated by filtration and dried in vacuo at 90° C.

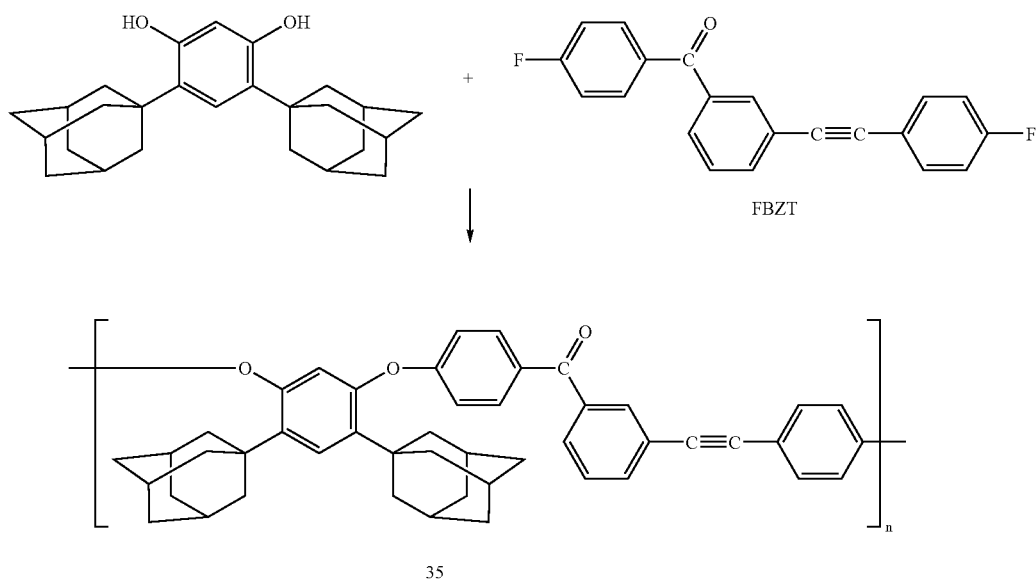

Example 2

Synthesis of Alternative Polymers

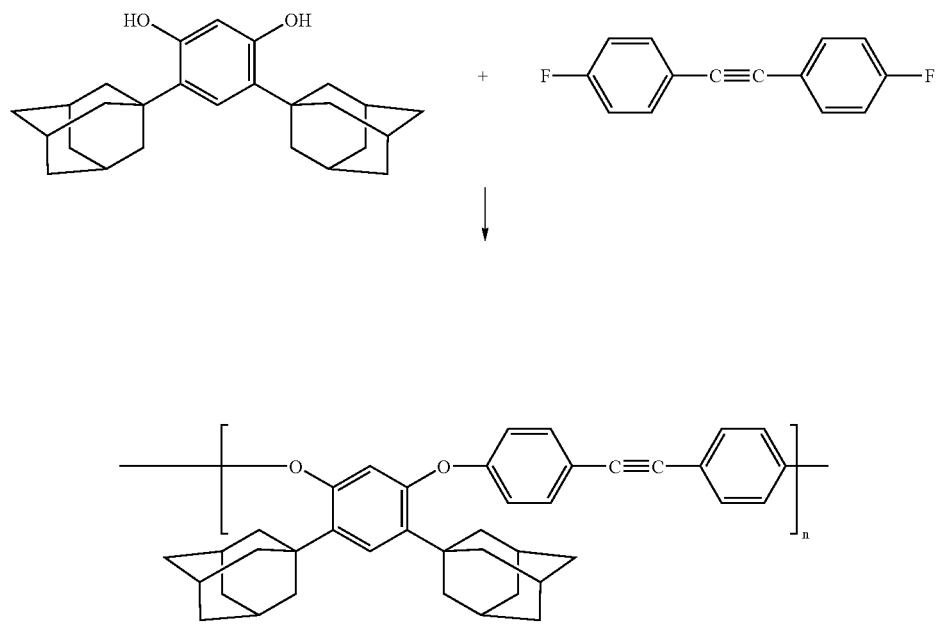

The synthetic procedure for backbone 1 follows the procedure as described in Example 1, but employs 4,4'-difluorotolane as the difluoro compound.

Example 2A

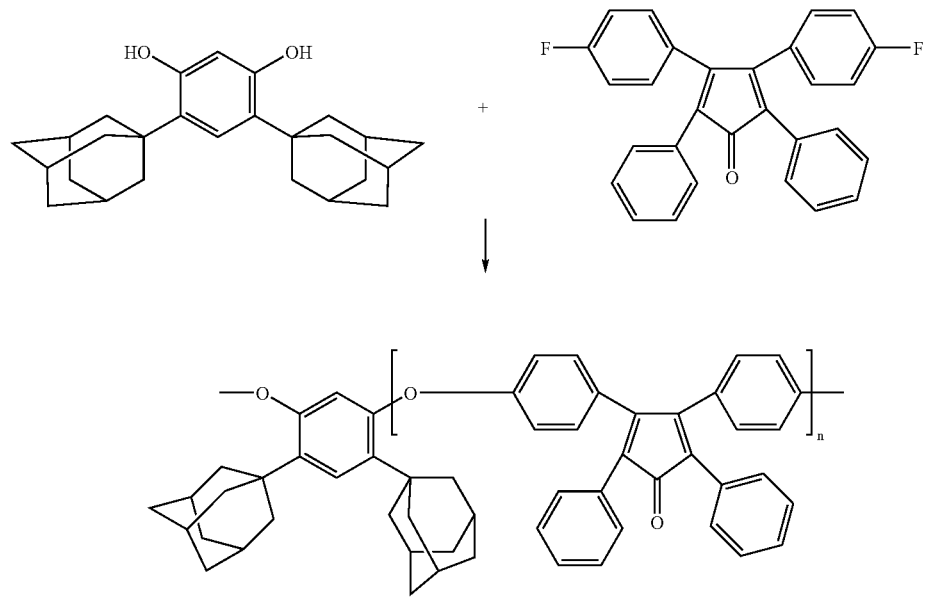

The synthetic procedure of Example 1 is followed except that 3,4-difluorotetraphenylcyclodienone is used as the difluoro compound.

Example 3

Contemplated Alternative Backbones

The following structures are contemplated exemplary backbones that can be fabricated according to the general synthetic procedure in Examples 1 and 2.

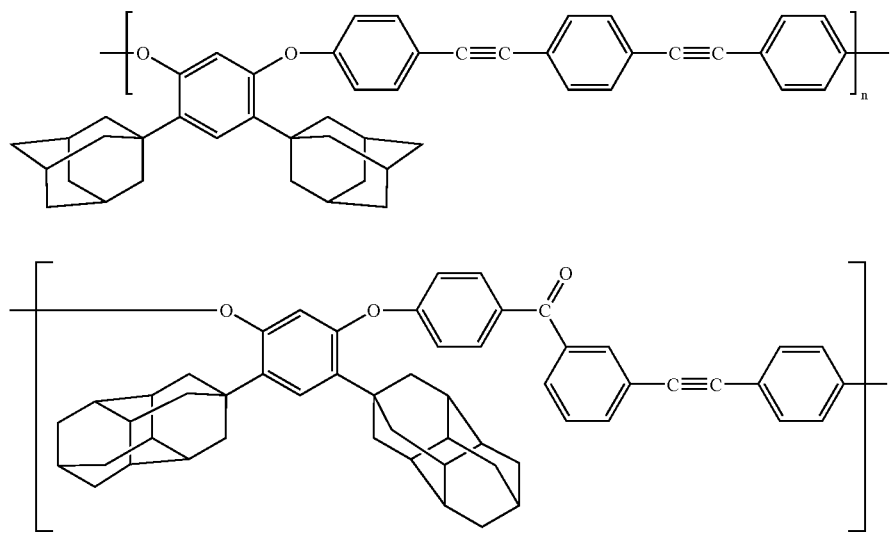

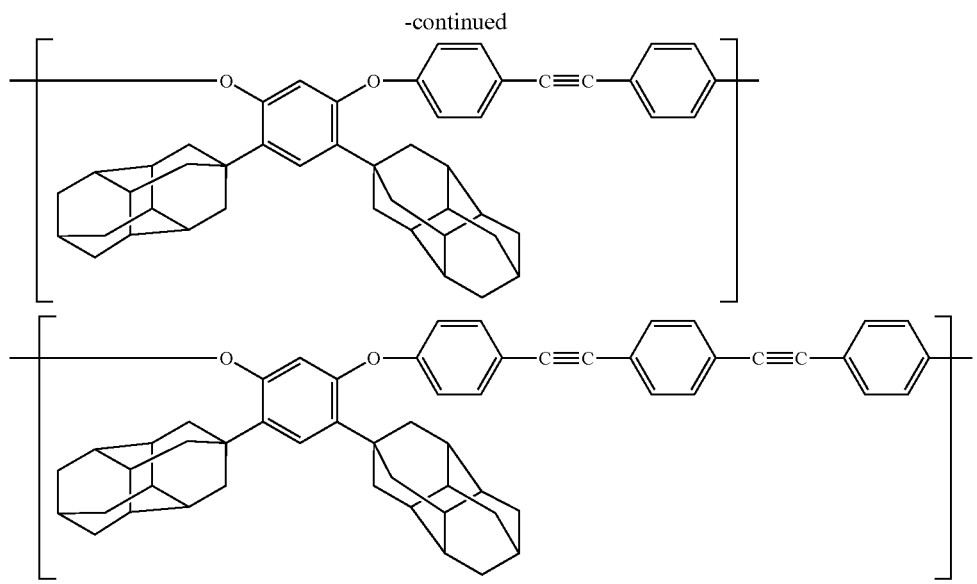

Example 4

Adamantanyl endcapped monomers as shown in FIGS. 5A and 5B were synthesized as described in C. M. Lewis, L. J. Mathias, N. Wiegal, ACS Polymer Preprints, 36(2), 140 (1995).

Example 5

Synthesis of 1,3,5,7-Tetrabromoadamantane (TBA)

1,3,5,7-Tetrabromoadamantane synthesis started from commercially available adamantane and followed the synthetic procedures as described in G. P. Sollott and E. E. Gilbert, J. Org. Chem., 45, 5405–5408 (1980), B. Schartel, V. Stümpflin, J. Wendling, J. H. Wendorff, W. Heitz, and R. Neuhaus, Colloid Polym. Sci., 274, 911–919 (1996), or A. P. Khardin, I. A. Novakov, and S. S. Radchenko, Zh. Org. Chem., 9, 435 (1972). Quantities of up to 150 g per batch were routinely synthesized.

Synthesis of 1,3,5,7-Tetrakis(3/4-bromophenyl)adamantane (TBPA)

In a first step, TBA was reacted with bromobenzene to yield 1,3,5,7-tetrakis(3/4-bromophenyl)adamantane (TBPA) as described in *Macromolecules*, 27, 7015–7023 (1994) (supra). HPLC-MS analysis showed that of the total reaction product the percentage of the desired TBPA present was approximately 50%, accompanied by 40% of the tribrominated tetraphenyl adamantane and about 10% of the dibrominated tetraphenyladamantane.

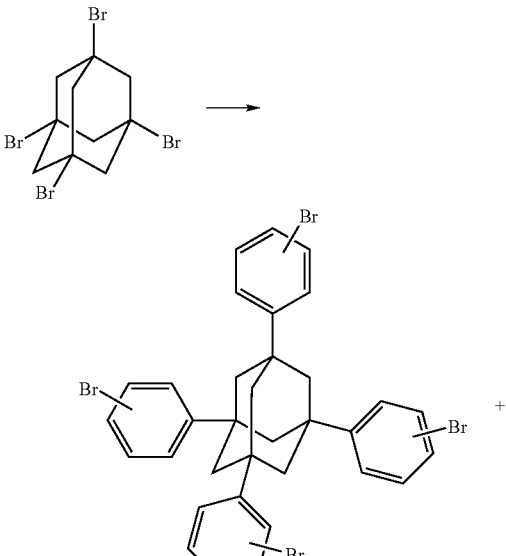

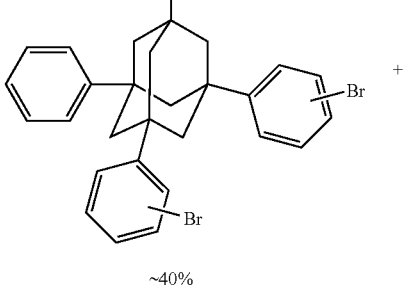

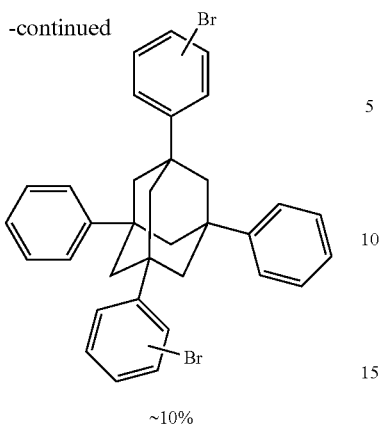

~10%

Specifically, the Experimental Procedure for the above is as follows:

Equipment:

1. Dry 5L 3-neck round bottom flask. 2. Water condenser. 3. Magnetic stir-bar. 4. Heating mantle. 5. Thermocouple. 6. Thermal controller unit. 7. $N_2$ inlet-outlet to 30% KOH solution. Assemble above equipment and Purge flask with $N_2$ for 10 min.

Procedure:

Weigh 160.00±0.30 g of TBA and 4,800.00±1.0 g of Bromobenzene. Total volume is 3220 mL and d=1.49. Weigh 32.25±0.30 g of Aluminum Bromide. Pour 2 L (62% v/v from total volume) of bromobenzene into flask. Activate stir-bar.

Add full amount of TBA and rinse funnel with 1 L (31% v/v from total volume) of bromobenzene. Take HPLC sample of starting material. Compare with standard HPLC chromatogram.

Add full amount of aluminum bromide to solution and rinse funnel with 220 mL (7% v/v from total volume) of bromobenzene. Solution at this point should be dark purple with no precipitation visible. Stir the reaction mixture for 1 h at room temperature.

After 1 h, raise temperature of reaction mixture to 40° C. After temperature reaches 40° C., stir reaction mixture for 3 hr. Take HPLC sample at time 1+3.0, respectively, at 40° C. Note: The reaction is judged to be over if no traces of TBA are seen on HPLC chromatogram.

When reaction is over, pour the dark reaction mixture into a 20 L pail containing 7 L (217% v/v relative to the total volume of bromobenzene) D.I. Water, 2 L (62% v/v relative to the total volume of bromobenzene) ice, and 300 mL (37%) HCl (9% v/v relative to the total volume of bromobenzene). Stir vigorously using an overhead-stirrer for 1 hr±10 min.

Transfer the organic layer to a separatory chamber and wash it 2 times with 700 mL (22% v/v relative to the total volume of bromobenzene) portions of de-ionized water. Place the washed organic layer in a 4L separatory funnel and add it, as a slow stream, to 16 L (5×times to the total volume of bromobenzene) methanol, in a 30 L pail placed under and overhead-stirrer, to precipitate a solid during 25 min±5 min.

After addition is complete, agitate the methanol suspension vigorously during 1 hr±10 min. Filter the methanol suspension by suction through a Buchner funnel (185 mm). Wash the solid on filter cake with three portions of 600 mL (19% v/v relative to the total volume of bromobenzene) methanol. Let the solid suction dry for 30 min.

Empty the pinkish powder into a crystallizer dish using a spatula and place it in a vacuum-oven to dry overnight. Weigh after drying. Re-dry in the vacuum-oven for 2 additional hours and re-weight. Continue drying, if necessary, until weight change is <1%. After solid is dry, record the final weight and calculate yield. Expected Yield is 176.75–192.80 g (66–72%).

Unexpectedly, however, when the product mixture was subjected to fresh reagent and catalyst (bromobenzene and $AlCl_3$, 1 min at 20° C.), TBPA was obtained in yields of approximately 90–95%. We were so astonished by this result that we repeated it several times to confirm and this resulted in the present process for converting the preceding mixture to a useful product, as shown below and in FIG. 11.

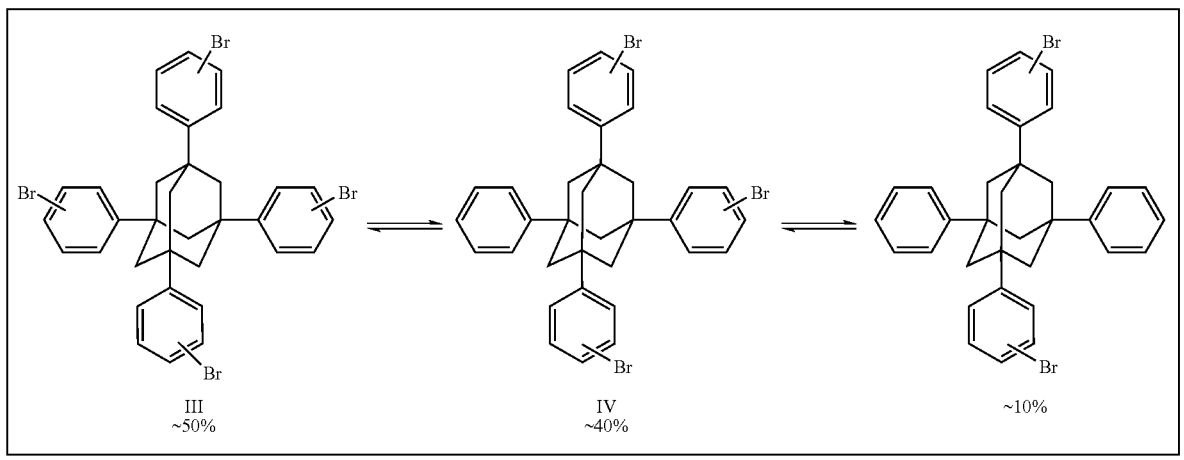

(mixture of p-, m-isomers of four- and tri-bromoderivatives)

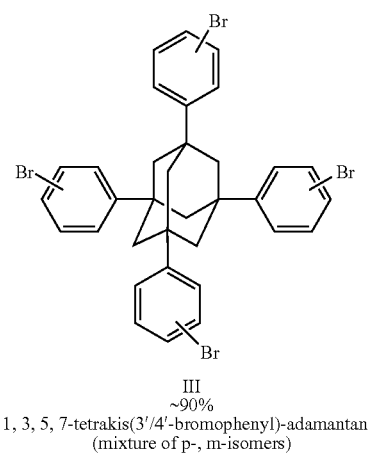

III ~90%
1,3,5,7-tetrakis(3'/4'-bromophenyl)-adamantane,
(mixture of p-, m-isomers)

Specifically, the Experimental Procedure for the above is as follows:

Equipment:
1. Dry 5 L 3-neck round bottom flask. 2. Water condenser. 3. Magnetic stir-bar. 4. Heating mantle. 5. Thermocouple. 6. Thermal controller unit. 7. $N_2$ inlet-outlet to 30% KOH solution. Assemble above equipment and Purge flask with $N_2$ for 10 min.

Procedure:
Calculate the corresponding amounts of bromobenzene and aluminum bromide needed based on the yield of the TBPA synthesized in the above/conventional synthesis.

Pour the appropriate amount (80% v/v from the total volume) of bromobenzene into flask. Activate stir-bar.

Add full amount of TBPA from the previous synthesis and rinse funnel with appropriate amount (10% v/v from the total volume) of bromobenzene.

Take HPLC sample of starting material. Compare with standard HPLC chromatqgram.

Add full amount of aluminum bromide to the solution and rinse funnel with remainder (10% from the total volume) of bromobenzene. Solution at this point should be dark purple with no precipitation visible.

Stir the reaction mixture for 17 min at room temperature. Take HPLC sample after 5 min. Take HPLC sample after 17 min.

Note: The reaction is judged to be over when the group of peaks corresponding to TBPA was dominant in the HPLC chromatogram.

When reaction is over, pour the dark reaction mixture into a 20L pail containing 7 L (217% v/v relative to the total volume of bromobenzene) D.I. Water, 2 L (62% v/v relative to the total volume of bromobenzene) ice, and 300 mL (37%) HCl (9% v/v relative to the total volume of bromobenzene).

Stir vigorously using an overhead-stirrer for 1 hr±10 min.

Transfer the organic layer to a separatory chamber and wash it 2 times with 700 mL (22% v/v to the total volume of bromobenzene) portions of D.I. water and 3 times with 700 mL (22% v/v relative to the total volume of bromobenzene) portions of saturated NaCl solution.

Place the washed organic layer in a 4 L separatory funnel and add it, as a slow stream, to the appropriate amount (5× times to the total volume of bromobenzene) methanol, in a 30 L pail placed under and overhead-stirrer, to precipitate a solid during 25 min±5 min.

After addition is complete, agitate the methanol suspension vigorously during 1 hr±10 min.

Filter the methanol suspension by suction through a Buchner funnel (185 mm).

Wash the solid on filter cake with three portions of 600 mL (19% v/v relative to the total amount of bromobenzene) methanol.

Let the solid suction dry for 30 min.

Empty the pinkish powder into a crystallizer dish using a spatula and place it in an oven to dry overnight. Weigh after drying. Re-dry in the vacuum-oven for 2 additional hours and re-weigh. Continue drying, if necessary, until weight change is <1%. After solid is dry, record the final weight and calculate yield. The expected yield is 85–91%.

Synthesis of
1,3,5,7-Tetrakis(phenylethynylphenyl)adamantane
(TPEPA)

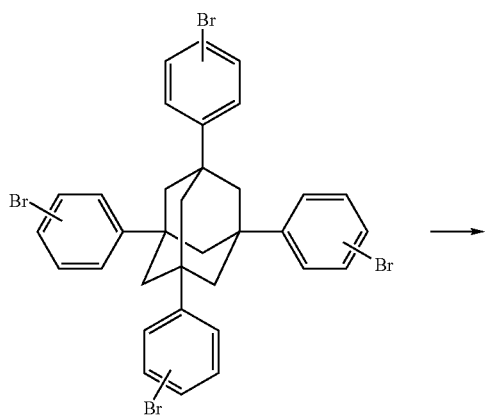

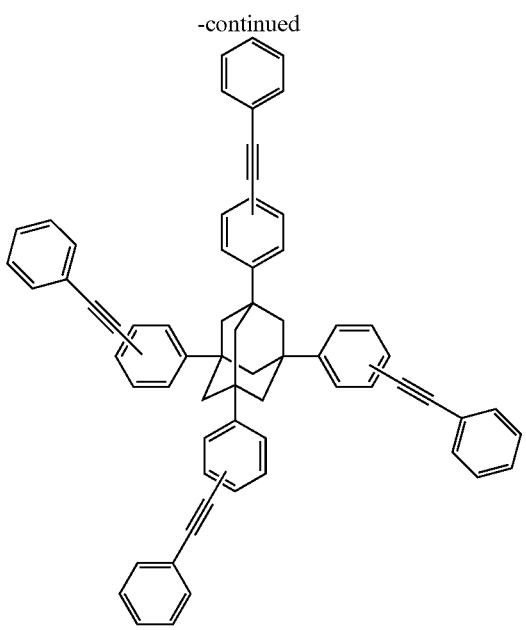

TBPA was reacted with phenylacetylene to yield the final product 1,3,5,7-tetrakis[(3,4-phenylethynyl)phenyl)]adamantane (TPEPA)—as a mixture of isomers—following a general reaction protocol for a palladium-catalyzed Heck ethynylation. TPEPA made from the reaction including TBPA is soluble in cyclohexanone. TPEPA can also be made from 1,3,5,7-tetrakis(4-iodophenyl)adamantane (TIPA) instead of TBPA. When TPEPA is made from TIPA, it is insoluble in cyclohexanone.

Specifically, the procedure for this step is as follows:

Equipment:
1. Dry 2 L 3-neck round bottom flask. 2. Water condenser. 3. Overhead-Stirrer. 4. Heating mantle. 5. Thermocouple. 6. Thermal controller unit. 7. Dropping funnel 8. 2-necked adapter. 9. $N_2$ inlet-outlet to 30% KOH solution. Assemble above equipment and Purge flask with $N_2$ for 10 min.

Procedure:

Weigh TBPA from second synthesis procedure from above.

Calculate amount needed for each of the following compounds: a) Phenylacetylene; b) $(Ph_3P)_2PdCl_2$; c) Triphenylphosphine; d) Copper(I) Iodide; and e) Triethylamine.

Add the appropriate amount of Triethylamine (Total volume from 1-e minus 300 mL) to the reaction flask and activate the overhead stirrer, follow it by the addition of the following compounds in the order listed below:

$(Ph_3P)_2PdCl_2$, rinse the funnel with 50 mL (4% of total volume) of triethylamine (TEA) and stir for 5 min.

Triphenylphosphine, rinse the funnel with 50 mL (4% of total volume) TEA, stir for 5 min.

Copper(I) Iodide, rinse the funnel with 50 mL (4% of total volume) TEA, stir for 5 min.

Add the total amount of TBPA from the second TBPA synthesis above and rinse the funnel with 100 mL (8% of total volume) TEA. Start heating the flask to 80° C.

Place the measured quantity of Phenylacetylene diluted with 50 mL (4% of total volume) TEA in the dropping funnel, mounted on one neck of the 2-necked adapter.

Once the temperature of the reaction mixture reaches 80° C., take a sample for HPLC analysis. This is the starting material.

Add the diluted phenylacetylene dropwise to the reaction mixture over 30 min±10 min.

Note: This is an exothermic reaction. Control the temperature by using a water bath.

Continue heating for 3 hours. The reaction is stopped after 3 hours of heating at 80° C.

Take an HPLC sample at time 3 hour at 80° C.

Cool the reaction mixture to 50° C. then filter through a Buchner funnel. (185 mm). Wash the crude solids 2 times with 600 mL of TEA. (v/v%=52% relative to 1-e)

Load filter cake to a 4 L beaker and stir the contents with 1 L (v/v %=87% relative to 1-e) of TEA for 15 min at room temperature.

Filter through a Buchner funnel (185 mm) and wash the crude solids 2 times with 300 mL TEA. (v/v %=26% relative to 1-e)

Suction dry the solids overnight.

Note: Take 3 g of crude product for (TLC, HPLC, DSC, Trace Metals, UV-VIS) analysis.

Figure 11:
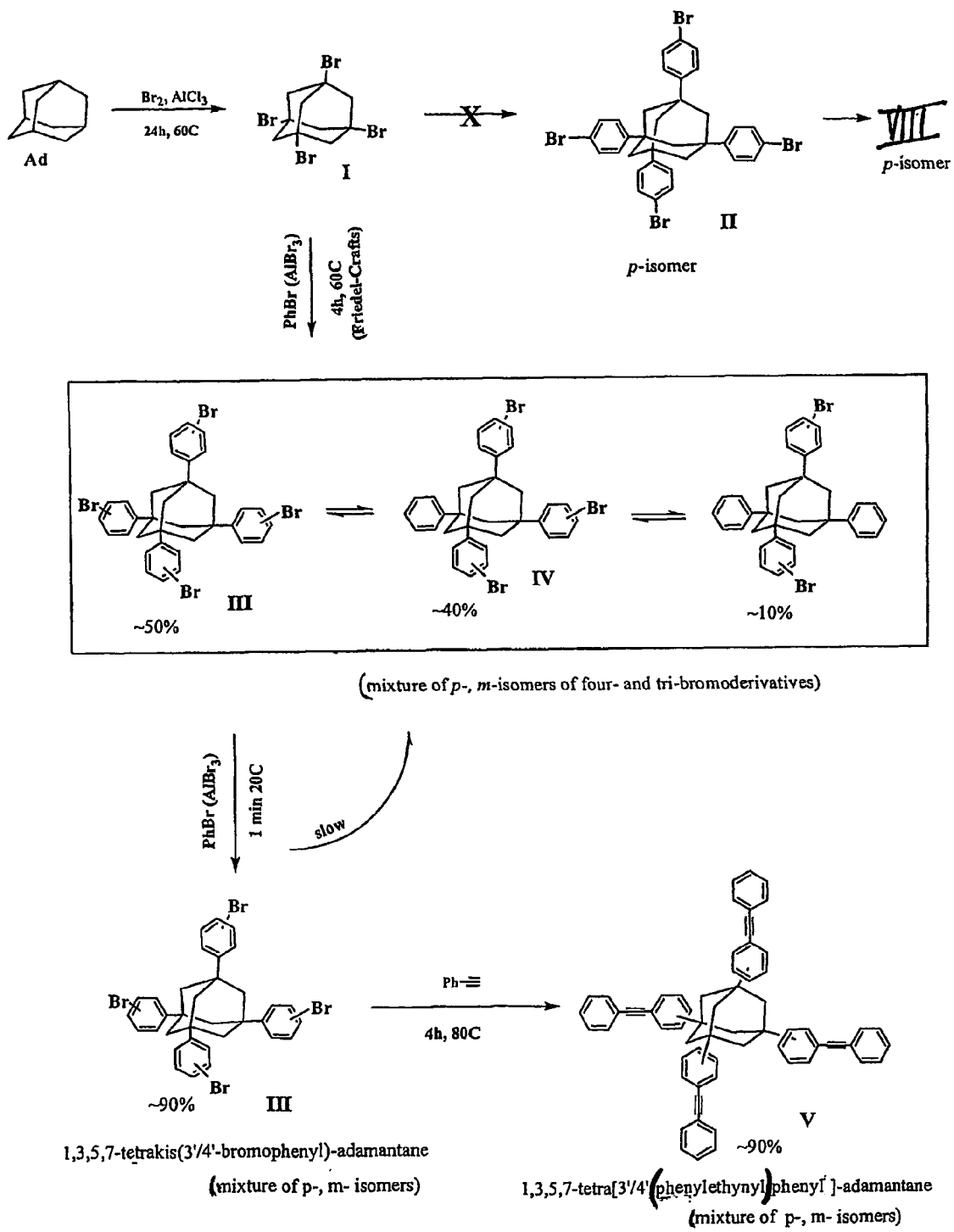
FIG. 11 is a synthetic scheme for the preparation of an isomeric mixture of thermosetting monomers.
Figure 12:
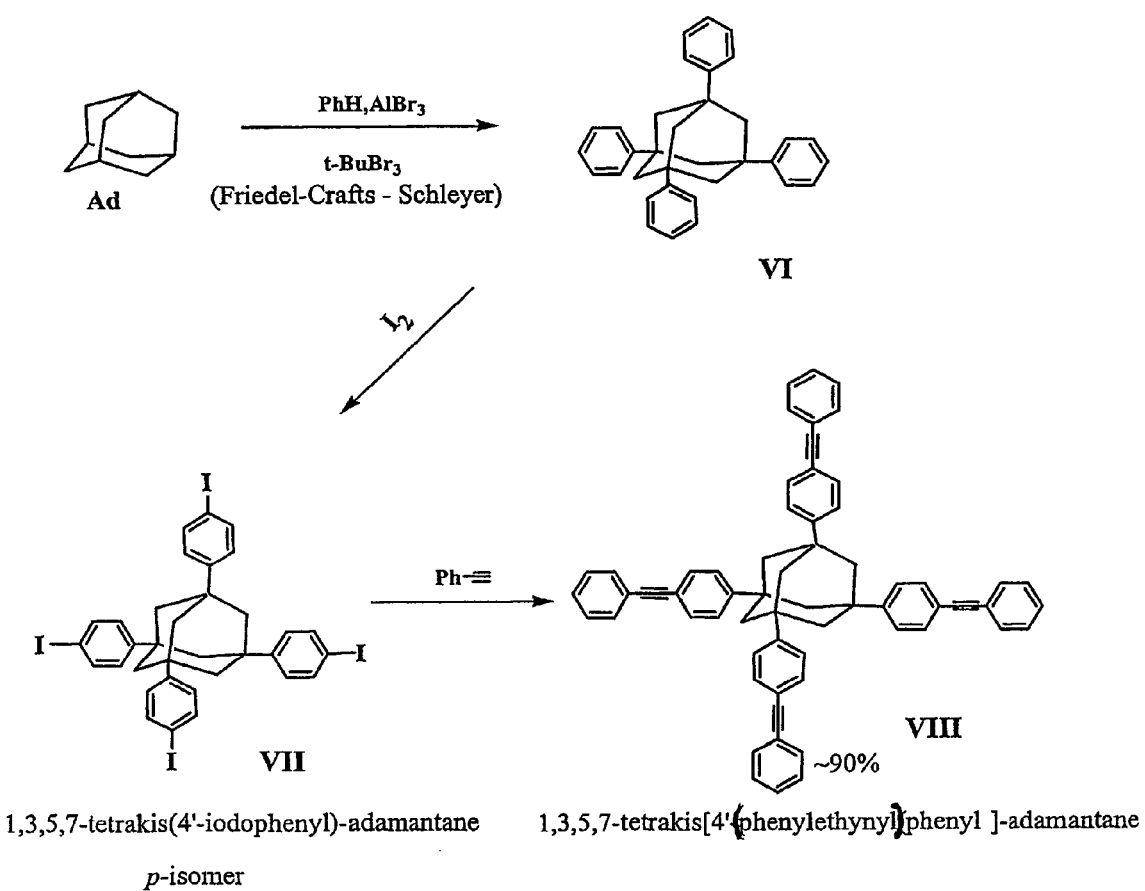
FIG. 12 is a synthetic scheme for the preparation of 1,3,5,7-tetrakis[4'-(phenylethynyl)phenyl]adamantane (p-isomer).

As mentioned briefly in the Background section, Reichert's goal was to prepare 1,3,5,7-tetrakis[(4-phenylethynyl)phenyl)]adamantane of definite structure, namely, single p-isomer of this compound—1,3,5,7-tetrakis[4'-(phenylethynyl)phenyl]-adamantane (VII). This, and only this compound, having definite structure (which can be characterized by the analytical methods) was the target of Reichert's work. Please note that FIGS. 11 and 12 show the preparation of the isomers discussed below, and the Roman numerals in the text of this Example correspond with the Roman numerals in FIGS. 11 and 12.

Reichert's plan was to realize the following sequence:

1,3,5,7-tetrabromoadamantane (I)→1,3,5,7-tetrakis(4'-bromophenyl)-adamantane (II)(p-isomer)→1,3,5,7-tetrakis[4'-(phenylethynyl)phenyl)]-adamantane (VIII) (p-isomer)

Reichert failed on step (I)→(II) in that she thought she obtained 1,3,5,7-tetrakis(3'/4'-bromophenyl)-adamantane (III)—a mixture of isomers of 1,3,5,7-tetrakis(bromophenyl)-adamantane, containing the combination of p- and m-bromophenyl groups attached to adamantane core (see below), and she considered the goal of her work not fulfilled. As support for this she writes: "The lack of regioselection during arylation discouraged us from attempting further Friedel-Crafts reactions on adamantane and lead to further study of the derivatization of the easily formed 1,3,5,7-tetraphenyladamantane" (VI). To prepare single p-isomer—1,3,5,7-tetrakis[4'-(phenylethynyl)phenyl)]-adamantane (VIII) she designed a "detour procedure", as follows:

1,3,5,7-tetraphenyladamantane (VI)→1,3,5,7-tetrakis(4'-iodophenyl)-adamantane (VII)→1,3,5,7-tetrakis[4'-phenylethynyl(phenyl)]-adamantane (VIII)

Reichert successively realized this sequence, and isolated the single p-isomer (VIII), but the solubility of this compound turned out to be so low, that she was not able to obtain $^{13}C$ NMR spectra of this compound. Reichert observes: "Compound 3 [(VIII)] was found to be soluble enough in chloroform that a $^1H$ NMR spectrum could be obtained. However, acquisition times were found impractical for obtaining a solution $^{13}C$ NMR spectrum. Solid-state NMR was used to identify the product" Reichert. Diss.(supra). And to confirm these results, Reichert's compound was tested with several standard organic solvents and was found to be essentially insoluble in every one of the tested organic solvents.

So, in other words, Reichert prepared what she thought was 1,3,5,7-tetrakis(3'/4'-bromophenyl)adamantane (III), but did not continue in this direction, because this product was not a single isomer with definite structure. Instead she prepared single isomer of 1,3,5,7-tetrakis(4'-iodophenyl) adamantane (VII), and transformed it into single isomer of 1,3,5,7-tetrakis[4'-(phenylethynyl)phenyl]adamantane (VIII), which turned out to be insoluble, and (because of that) not useful.

We repeated the reaction of 1,3,5,7-tetrabromoadamantane with bromobenzene numerous times and our analysis of product of reaction of 1,3,5,7-tetrabromoadamantane with bromobenzene showed that it is not 1,3,5,7-tetrakis(3'/4'-bromophenyl)adamantane (III) (as Reichert suggested), but a mixture of 1,3,5,7-tetrakis(3'/4'-bromophenyl)adamantane (III) with approximately equal quantity of 1-phenyl-3,5,7-tris(3'/4'-bromophenyl)adamantane (IV). This conclusion was confirmed by LC-MS study and elemental analysis.

We were able to find the cause of such reaction course. Bromobenzene is known to disproportionate essentially in the conditions of Friedel-Crafts reaction (G. A. Olah, W. S. Tolgyesi, R. E. A. Dear. J. Org. Chem., 27, 3441–3449 (1962)):

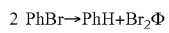

When benzene concentration in the reaction mixture increases, it begins to replace bromine in (I) [or bromophenyl in (III)]; benzene proportion is so high, that fast established equilibria leads to approx. equal quantities of (III) and (IV).

Therefore, Reichert did not obtain (as she thought) 1,3, 5,7-tetrakis(3'/4'-bromophenyl)adamantane (III); instead, she had approx. 1:1 mixture of 1,3,5,7-tetrakis(3'/4'-bromophenyl)adamantane (III) with 1-phenyl-3,5,7-tris(3'/4'-bromophenyl)adamantane (IV).

To shift equilibria toward 1,3,5,7-tetrakis(3'/4'-bromophenyl)adamantane (III) side, we treated solid product of reaction of 1,3,5,7-tetrabromoadamantane with bromobenzene [1:1 mixture of 1,3,5,7-tetrakis(3'/4'-bromophenyl)adamantane (III) and 1-phenyl-3,5,7-tris(3'/4'-bromophenyl)adamantane (IV)] by a new portion of brornobenzene in presence of aluminum bromide. It turned out that pure bromobenzene immediately replaces phenyl group in 1-phenyl-3,5,7-tris(3'/4'-bromophenyl)-adamantane (IV), so the product in solution in 30 seconds contains ~90–95% 1,3,5, 7-tetrakis(3'/4'-bromophenyl)-adamantane (III). This situation is conserved for ~5–10 min at room temperature, after which slowly increasing concentration of benzene leads to increase of 1-phenyl-3,5,7-tris(3'/4'-bromophenyl)-adamantane (IV) concentration, and in several hours equilibria is re-established with ~equal concentration of 1,3,5,7-tetrakis (3'/4'-bromophenyl)-adamantane (III) and 1-phenyl-3,5,7-tris(3'/4'-bromophenyl)-adamantane (IV).

Therefore, 1,3,5,7-tetrakis(3'/4'-bromophenyl)-adamantane (III) (that Reichert thought she synthesized) can be prepared by second treatment of the solid product of reaction of 1,3,5,7-tetrabromoadamantane with bromobenzene in presence of aluminum bromide.

1,3,5,7-tetra(3'/4'-bromophenyl)adamantane (III) subjected to Heck reaction with phenylacetylene gave novel 1,3,5,7-tetra[(3'/4'-phenylethynyl)phenyl]adamantane (V) (mixture of p- and m-isomers) which was confirmed by NMR and HPLC and is very well soluble in toluene, xylenes, cyclohexanone, anisole, propylene glycol methyl ether acetate, mesitylene, cyclohexylacetate, etc. For example, its solubility in cyclohexanone is >20%. This necessary property makes possible its ability to be spin coated, which ensures practical use of this material, especially in the field of layered materials and semiconductors.

Therefore, our prepared intermediate 1,3,5,7-tetra(3'/4'-bromophenyl)adamantane (III), gave us the opportunity to make 1,3,5,7-tetra[(3'/4'-phenylethynyl)phenyl]adamantane (V) (soluble mixture of p- and m-isomers), which can be used as spin-on low k dielectric material.

Example 6

Synthesis of m- and p-bromotolane Isomers

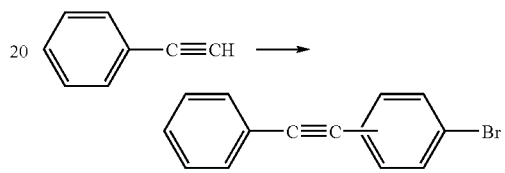

In a 500-mL 3-neckround-bottom flask, equipped with an addition funnel and a nitrogen gas inlet, 4-iodobromobenzene (25.01 g, 88.37 mmol.), triethylamine (300 mL), bis (triphenylphosphine)paladium[II] chloride (0.82 g) and cop-per[I]iodide (0.54 g) were added. Then, a solution of phenylacetylene (9.025 g, 88.37 mmol.) in triethylamine (50 mL) was added slowly, and the temperature of the solution was kept under 35C under stirring. The mixture was stirred for another 4 hours after addition was completed. The solvent was evaporated on the rotary evaporator and the residue was added to 200 mL of water. The product was extracted with dichloromethane (2×150 mL). The organic layers were combined and the solvents were removed by rotary evaporator. The residue was washed with 80 mL hexanes and filtered. TLC and HPLC showed a pure product (yield, 19.5 g, 86%). Additional purification was performed by short silica column chromatography (Eluent is 1:2 mixture of toluene and hexanes). A white crystalline solid was obtained after solvent removal. The purity of the product was characterized by GC/MS in acetone solution, and further characterized by proton NMR.

Synthesis of m- and p-Ethynyltolane

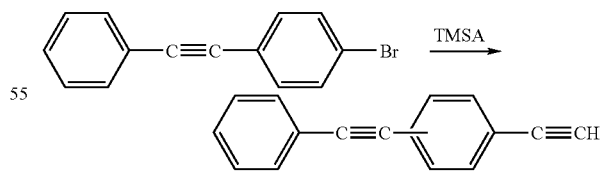

The synthesis of p-ethynyltolane from p-bromotolane was performed in two steps. In the first step, p-bromotolane was trimethylsilylethynylated using trimethylsilylacetylene (TMSA, as shown above), and in the second step, the reaction product of the first step was converted to the final end product.

Step 1 (Trimethylsilylethynylation of 4-bromotolane): 4-Bromotolane (10.285 g, 40.0 mMol), ethynyltrimethylsilane (5.894 g, 60.0 mMol), 0.505 g (0.73 mMol) of dichlorobis(triphenylphosphine)palladium[II] catalyst, 40 mL of anhydrous triethylamine, 0.214 g (1.12 mMol) of copper[I] iodide, and 0.378 g (1.44 mMol) of triphenylphosphine were placed into the $N_2$ purged, 5-Liter 4-neck round-bottom flask, equipped with an overhead mechanical stirrer, condenser, and positioned inside a heating mantle. The mixture was heated to a gentle reflux (about 88° C.) and maintained at reflux for 1.5 hours. The reaction mixture became a thick black paste and was cooled. Thin-layer chromatographic analysis indicated complete conversion of starting material 4-bromotolane to a single product. The solids were filtered and washed with 50 mL of triethylamine, mixed with 400 mL of water and stirred for 30 minutes. The solids was filtered and washed with 40 mL of methanol. The crude solid was recrystallized from 500 mL of methanol. On standing, lustrous silver colored crystals settled out. They were isolated by filtration and washed with 2×50 mL of methanol. 4.662 g was recovered (42.5% yield).

Step 2 (Conversion of 4-(Trimethylsilyl)ethynyltolane to 4-Ethynyltolane): To a 1-Liter 3 neck round-bottom flask equipped with a nitrogen inlet, an overhead mechanical stirrer, was charged 800 mL of anhydrous methanol, 12.68 g (46.2 mMol) of 4-(trimethylsilyl)ethynyltolane, and 1.12 g of anhydrous potassium carbonate. The mixture was heated to 50° C. Stirring continued until no starting material is detected by HPLC analysis (about 3 hours). The reaction mixture was cooled. The crude solids were stirred in 40 mL of dichloromethane for 30 min and filtered. The filtered suspended solids by HPLC showed mainly impurities. The dichloromethane filtrate was dried and evaporated to yield 8.75 g of a solid. On further drying in an oven, the final weight was 8.67 g, which represented a yield of 92.8%.

Synthesis of 1,3,5,7-tetrakis[(3'/4'-bisphenylethynyl)phenyl)]admantane(TBPEPA)

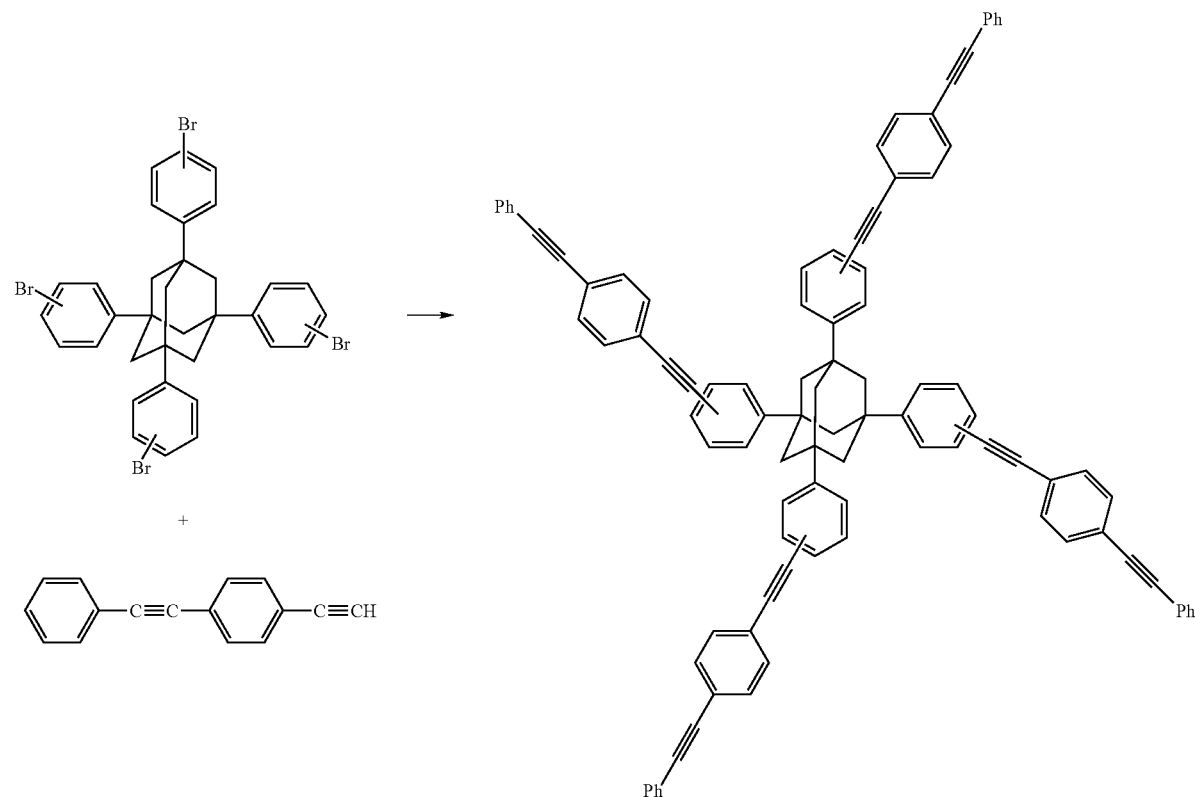

TBPA (supra) was reacted with 4-ethynyltolane to yield the final product 1,3,5,7-tetrakis-{3'/4'-[4"-(phenylethynyl)phenylethynyl]phenyl}adamantane (TBPEPA) following a general protocol for a palladium-catalyzed Heck ethynylation reaction.

The so prepared TBTA was dissolved in cyclohexanone to obtain a 10% (by weight) solution, 5 ml of which were spun onto two silicon wafers using standard procedures well known in the art. The TBTA was polymerized on the wafer by heating to a temperature of about 300° C., and cured at a temperature of 400° C. for 1 hour. The k-value was determined to be 2.57. It should be especially appreciated that when the k-value was compared to the k-value of TPEPA, (which is a structural analog to TBTA with a shortened length of the arms) the k-value of TPEPA was higher at about 2.60. Thus, the contemplated decrease in the k-value due to an increased length of the arms extending from the cage compound has been experimentally confirmed.

Example 7

Film Studies of TPEPA Produced from a TBPA Precursor (Example 6)

TPEPA (approx. 10 g or more) was dissolved in cyclohexanone (CHN) as 12% solution. The resulting solution was spun onto silicon wafers and then baked and cured into a film. The dielectric constant was measured to be around 2.60 with a Tg greater than or equal to 420° C. There was no shrinkage of the film and no IR changes after baking the film for 20 hours at 400° C.

Typical or representative spin coating conditions are shown below:

| Step | Process | Spin (RPM) | Time (Sec) |
|------|---------|------------|------------|
| 1 | Dispense | 0 | 2.8 |
| 2 | Delay | 0 | 1.7 |
| 3 | Spread | 1000 | 2 |
| 4 | Spin | 2000 | 40 |
| 5 | BSR | 1500 | 6 |
| 6 | EBR | 400 | 12 |
| 7 | EBR | 800 | 7 |
| 8 | Dry | 1000 | 7 |
| 9 | Dry | 1500 | 5 |
| 10 | End | 0 | 0.06 |

Pressurizing Gas: Helium
Dispense Pressure: 0.08 Mpa
Dispense Rate: 1.0 mL/sec
Inline Filter: 0.1 microns, PFFV01D8S (Millipore, Fuluoroline-S)
Coater: DNS SC-W80A-A VFDLP
Typical Bake and Cure Conditions for Contemplated Compounds
Bake Condition: 150–200–250° C., 1 minute each under nitrogen gas (<50 ppm oxygen)
Furnace Cure Condition: Typical 400° C. for 60 minutes in nitrogen (15 Lmin); Ramping up from 250° C. at 5K/min; Cure temperature range from 350–450° C.
Hot Plate Cure Condition: (as an alternate to furnace cure) 350–450° C. for 1–5 minutes in nitrogen.
Physical Properties of a Contemplated Compound:
Refractive Index:
After Bake: 1.702
After Cure: 1.629
Thickness (Angstroms):
After Bake: 8449
After Cure: 9052
Thickness Change (Percent Change):
Bake to Cure: 7.1

Thus, specific embodiments and applications of compositions and methods to produce a low dielectric constant polymer have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. An isomeric thermosetting monomer mixture, comprising a soluble mixture of isomers, wherein the mixture comprises at least one monomer having the structure

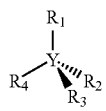

wherein Y is selected from a cage compound and a silicon atom, and $R_1$, $R_2$, $R_3$, and $R_4$ are independently selected from an aryl, a branched aryl, and an arylene ether, and wherein at least one of the aryl, the branched aryl, and the arylene ether has an ethynyl group.

2. The isomeric thermosetting monomer mixture of claim 1, wherein said Y is selected from the group consisting of adamantane and diamantane.

3. The isomeric thermosetting monomer mixture of claim 1, wherein said mixture comprises meta and para isomers.

4. A solvent having dissolved therein said isomeric thermosetting monomer mixture of claim 1.

5. The solvent of claim 4, wherein the solvent is cyclohexanone.

6. A spin-on polymer comprising the isomeric thermosetting monomer mixture of claim 1.

7. The spin-on polymer of claim 6, wherein the polymer has a dielectric constant of less than 3.0.

8. The spin-on polymer of claim 6, wherein the polymer has a dielectric constant of less than 2.7.

9. A thermosetting monomer having the structure

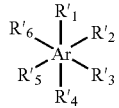

wherein Ar is an aryl, and $R'_1$, $R'_2$, $R'_3$, $R'_4$, $R'_5$, and $R'_6$ are independently selected from an aryl, a branched aryl, an arylene ether, and hydrogen, and wherein each of the aryl, the branched aryl, and the arylene ether have at least one ethynyl group.

10. A spin-on polymer comprising the thermosetting monomer of claim 9.

11. A method of producing a low dielectric constant polymer, comprising:
providing an isomeric thermosetting monomer mixture, comprising a soluble mixture of isomers, wherein the mixture comprises at least one monomer having the structure

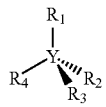

wherein Y is selected from a cage compound and a silicon atom, and $R_1$, $R_2$, $R_3$, and $R_4$ are independently selected from an aryl, a branched aryl, and an arylene ether, and wherein at least one of the aryl, the branched aryl, and the arylene ether has an ethynyl group; and polymerizing the thermosetting monomer mixture thereby forming the low dielectric constant polymer, wherein the polymerization comprises a chemical reaction of the ethynyl group.

12. The method of claim 11, wherein the Y is selected from the group consisting of an adamantane, and a diamantane.

13. The method of claim 11 wherein the aryl comprises a moiety selected from the group consisting of a phenylethynylphenyl, a phenylethynylphenylethynylphenyl, and a phenylethynylphenylphenyl.

14. The method of claim 11 wherein the arylene ether comprises a phenylethynylphenyl-phenyl ether.

15. The method of claim 11 wherein at least three of the aryl, the branched aryl, and the arylene ether have a ethynyl group, and wherein the polymerization comprises a chemical reaction of the at least three ethynyl groups.

16. The method of claim 11 wherein all of the aryl, the branched aryl, and the arylene ether have an ethynyl group, and wherein the polymerization comprises a chemical reaction of all of the ethynyl groups.

17. The method of claim 11 wherein the polymer comprises a poly(arylene ether).

18. The method of claim 11 wherein the step of polymerizing the thermosetting monomer mixture takes place without participation of an additional crosslinking molecule.

19. The method of claim 11 wherein said isomeric thermosetting monomer mixture comprises meta and para isomers.

20. The method of claim 11 wherein said isomeric thermosetting monomer mixture is dissolved in a solvent.

21. A method of producing a spin-on low dielectric constant polymer, comprising:

providing a thermosetting monomer having the structure

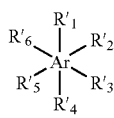

wherein Ar is an aryl, and R'$_1$, R'$_2$, R'$_3$, R'$_4$, R'$_5$, and R'$_6$ are independently selected from an aryl, a branched aryl, an arylene ether, and hydrogen, and wherein each of the aryl, the branched aryl, and the arylene ether have at least one ethynyl group; and polymerizing the thermosetting monomer thereby forming the low dielectric constant polymer, wherein the polymerization comprises a chemical reaction of the at least one ethynyl group.

22. The method of claim 21, wherein the aryl comprises a phenyl group.

23. The method of claim 21, wherein the step of polymerizing the thermosetting monomer into the polymer takes place without participation of a secondary molecule.

24. The method of claim 21, wherein the polymer comprises a poly(arylene ether).

25. An electrical device including a dielectric layer comprising a spin-on polymer, wherein the polymer is fabricated from an isomeric monomer mixture having at least one thermosetting monomer from the group comprising:

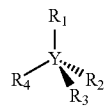

wherein Y is selected from a cage compound and a silicon atom, and R$_1$, R$_2$, R$_3$, and R$_4$ are independently selected from an aryl, a branched aryl, and an arylene ether, and wherein at least one of the aryl, the branched aryl, and the arylene ether has an ethynyl group;

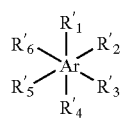

wherein Ar is an aryl, and R'$_1$, R'$_2$, R'$_3$, R'$_4$, R'$_5$, and R'$_6$ are independently selected from an aryl, a branched aryl, an arylene ether, and hydrogen, and wherein each of the aryl, the branched aryl, and the arylene ether have at least one ethynyl group.

26. The electrical device of claim 25, wherein said thermosetting monomer comprises an isomeric thermosetting monomer mixture.

27. The electrical device of claim 26, wherein said isomeric thermosetting monomer mixture comprises meta and para isomers.

28. The electrical device of claim 25, wherein said isomeric thermosetting monomer mixture is dissolved in a solvent.

29. A spin-on low dielectric constant material, comprising:

a first backbone having a first aromatic moiety and a first reactive group;

a second backbone having a second aromatic moiety and a second reactive group, wherein the first and second backbones are crosslinked via the first and second reactive groups in a crosslinking reaction; and a cage structure covalently and pendently bound to at least one of the first and second backbones, wherein the cage structure comprises at least eight atoms.

30. The low dielectric constant material of claim 29, wherein the crosslinking reaction takes place without a secondary crosslinker.

31. The low dielectric constant material of claim 29, wherein the aromatic moiety comprises a phenyl.

32. The low dielectric constant material of claim 29, wherein the aromatic moiety comprises an arylene ether.

33. The low dielectric constant material of claim 29, wherein the first backbone comprises a poly(arylene ether).

34. The low dielectric constant material of claim 29, wherein the first reactive groups comprises an electrophile.

35. The low dielectric constant material of claim 29, wherein the first reactive groups comprises an tetracyclone.

36. The low dielectric constant material of claim 29, wherein the second reactive groups comprises a nucleophile.

37. The low dielectric constant material of claim 29 wherein the second reactive groups comprises a phenylethynylphenyl group.

38. The low dielectric constant material of claim 29, wherein the first and second reactive groups are identical.

39. The low dielectric constant material of claim 29, wherein the reaction is a cycloaddition.

40. The low dielectric constant material of claim 31, wherein the cycloaddition is a Diels-Alder reaction.

41. The low dielectric constant material of claim 29, wherein the cage structure comprises at least one carbon atom.

42. The low dielectric constant material of claim 29, wherein at least one of the first reactive group or the second reactive group comprises an ethynyl group.

43. The low dielectric constant material of claim 29, wherein the cage structure comprises at least one of an adamantane and a diamantane.

44. The low dielectric constant material of claim 29, wherein the cage structure comprises a substituent.

45. The low dielectric constant material of claim 29, wherein the substituent is selected from the group consisting of a halogen, an alkyl, and an aryl.

46. The low dielectric constant material of claim 29, wherein the cage structure is covalently bound to the first and the second backbone.

47. The low dielectric constant material of claim 29, wherein the cage structure is covalently bound to at least one of the termini of the first and the second backbone.

48. A method of producing a low dielectric constant polymer, comprising the steps of:
providing a isomeric mixture of chemical reactants having the structure:

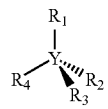

wherein Y is selected from a cage compound, and $R_1$, $R_2$, $R_3$, and $R_4$ are independently reactive groups;

converting the chemical reactant to a thermosetting monomer intermediate;

subjecting the thermosetting monomer intermediate to a fresh reagent solution and a fresh catalyst to produce a thermosetting monomer; and polymerizing the thermosetting monomer thereby forming the low dielectric constant polymer, wherein polymerizing comprises a chemical reaction of the reactive group.

49. The method of claim 48, wherein the reagent comprises bromobenzene and the catalyst comprises $AlBr_3$ or $AlCl_3$.

50. The method of claim 48, wherein the reagent comprises an aromatic or phenyl group and the catalyst is a Lewis Acid.

* * * * *